US005830706A

United States Patent [19]
Mascarenhas et al.

[11] Patent Number: 5,830,706
[45] Date of Patent: Nov. 3, 1998

[54] POLYPEPTIDE FUSIONS TO POLYPEPTIDES OF THE BETA-TREFOIL FOLD STRUCTURAL FAMILY

[75] Inventors: Desmond Mascarenhas, San Rafael; Yang Zhang, Sunnyvale; Pamela S. Olson, Cupertino; David R. Olsen, Menlo Park; Pedro A. Carrillo, San Francisco, all of Calif.

[73] Assignee: Celtrix Pharmaceuticals, Inc., Santa Clara, Calif.

[21] Appl. No.: 460,915

[22] Filed: Jun. 5, 1995

Related U.S. Application Data

[63] Continuation of Ser. No. 100,744, Aug. 2, 1993, Pat. No. 5,563,046.
[51] Int. Cl.⁶ ............................ C07K 19/00; C12N 15/62
[52] U.S. Cl. ................. 435/69.7; 435/252.3; 435/320.1; 530/350; 536/23.4
[58] Field of Search .............................. 435/69.7, 202.3, 435/320.1, 69.52; 536/23.4; 530/350

[56] References Cited

U.S. PATENT DOCUMENTS

| | | | |
|---|---|---|---|
| 4,595,658 | 6/1986 | Zinder et al. | 435/64.1 |
| 4,801,536 | 1/1989 | Stahl et al. | 435/69.1 |
| 5,084,384 | 1/1992 | Wong et al. | 435/69.4 |
| 5,143,830 | 9/1992 | Holland et al. | 435/69.7 |
| 5,496,924 | 3/1996 | Habermann et al. | 530/350 |

FOREIGN PATENT DOCUMENTS

| | | |
|---|---|---|
| WO 88/02406 | 4/1987 | WIPO. |
| WO 89/09829 | 10/1989 | WIPO. |
| WO 89/12678 | 12/1989 | WIPO. |
| WO 91/11454 | 8/1991 | WIPO. |
| WO 92/13955 | 8/1992 | WIPO. |

OTHER PUBLICATIONS

Williams et al., "Cytoplasmic inclusion bodies in *Escherichia coli* producing biosynthetic human insulin proteins" *Science* (1992) 215:687–689.

Schoner et al., "Isolation and purification of protein granules from *Escherichia coli* cells overproducing bovine growth hormone" *Bio/Technology* (Feb. 1985) pp. 151–154.

Goeddel et al., "Expression in *Escherichia coli* of chemically synthesized genes for human insulin" *Proc. Natl. Acad. Sci. USA* (1979) 76(1):106–110.

Furman et al., "Recombinant human insulin–like growth factor II expressed in *Escherichia coli*" *Bio/Technology* (Oct. 1987) 5:1047–1051.

di Guan et al., "Vectors that facilitate the expression and purification of foreign peptides in *Escherichia coli* by fusion to maltose–binding protein" *Gene* (1988) 67:21–30.

Johnson et al., "Vaccination against ovine cysticercosis using a defined recombinant antigen" *Nature* (1989) 338:585–587.

Miller et al., "Cloning and expression of a yeast ubiquitin–protein cleaving activity in *Escherichia coli*" *Bio/Technology* (1989) 7:698–704.

LaVallie et al., A thioredoxin gene fusion expression system that circumvents inclusion body formation in the *E. coli* cytoplasm *Bio/Technology* (1993) 11:187–193.

Schulz et al., "Increased expression in *escherichia coli* of a synthetic gene encoding human somatomedin C after gene duplication and fusion" *J. Bacteriol.* (Dec. 1987) pp. 5385–5392.

Tobias et al., "Cloning and functional analysis of ubiquitin–specific protease gene UPB1 of *saccharomyces cerevisiae*" *J. Biol. Chem.* (1991) 266(18):12021–12028.

Pugsley, "The complete general secretory pathway in gram–negative bacteria" *Microbiol. Rev.* (Mar. 1993) pp. 50–108.

Jacobson et al., "Properties of a major protein released from *Escherichia coli*" *Biochem.* (1976) 15(11):2298–2302.

Joseph–Liauzun et al., "Human recombinant interleukin–1β isolated from *Escherichia coli* by simple osmotic shock" *Gene* (1990) 86:291–295.

Nagahari et al., "Secretion into the culture medium of a foreign gene product from *Escherichia coli*: Use of the ompF gene for secretion of β–endorphin" *EMBO J.* (1985) 4(13a):3589–3592.

Kato et al., "Construction of an excretion vector and extracellular production of human growth hormone from *Escherichia coli*" *Gene* (1987) 54:197–202.

Holland et al., "Haemolysin secretion from *E. coli*" *Biochimie* (1990) 72:131–141.

Bardwell et al., "Identification of a protein required for disulfide bond formation in vivo" *Cell* (1991) 67:581–589.

Bayer, "Response of cell walls of *Escherichia coli* to a sudden reduction of the environmental osmotic pressure" *J. Bacteriol.* (Mar. 1967) pp. 1104–1112.

Chang et al., "Construction and characterizaton of amplifiable multicopy DNA cloning vehicles derived from the P15A cryptic miniplasmid" *J. Bacteriol.* (1978) pp. 1141–1156.

Cooper et al., "Evidence for export of a muscle lectin form cytosol to extracellular matrix and for a novel secretory mechanism" *J. Cell Biol.* (1990) 110:1681–1691.

Eisenberg et al., "Primary structure and functional expression from complementary DNA of a human interleukin–1 receptor antagonist" *Nature* (1990) 343:341–346.

Eisenberg et al., "Interleukin 1 receptor antagonist is a member of the interleukin 1 gene family: Evolution of a cytokine control mechanism" *Proc. Natl. Acad. Sci. USA* (1991) 88:5232–5236.

(List continued on next page.)

*Primary Examiner*—John Ulm
*Attorney, Agent, or Firm*—Morrison & Foerster,LLP

[57] ABSTRACT

The invention is directed to the use of IL-1-like fusion polypeptides to increase the solubility and activity of recombinant polypeptides. The invention includes a nucleic acid encoding a fusion polypeptide comprising an interleukin-1-like polypeptide and a polypeptide of interest and the method of using such a nucleic acid to produce recombinant fusion polypeptides.

16 Claims, 11 Drawing Sheets

OTHER PUBLICATIONS

Engler et al., "Cloning of authentic human epidermal growth factor as a bacterial secretory protein and its initial structure–function analysis by site–directed mutagenesis" *J. Biol. Chem.* (1988) 263(25):12384–12390.

Habazetti et al., "Structure of hisactophilin is similar to interleukin–1β and fibroblast growth factor" *Nature* (1992) 359:855–858.

Hsiung et al., "High level expression, efficient secretion and folding of human growth hormone in *Escherichia coli*" *Bio/Technology* (1986) 4:991–995.

Kamitani et al., "Identification and characterization of an *Escherichia coli* gene required for the formation of correctly folded alkaline phosphatase, a periplasmic enzyme" *Embo J.* (1992) 11:57–62.

Kellenberger, "The 'bayer bridges' confronted with results from improved electron microscopy methods" *Mol. Microbiol.* (1990) 4(5):697–705.

Lunn et al., "Localization of thioredoxin from *Escherichia coli* in an osmotically sensitive compartment" *J. Biol. Chem.* (1982) 257(19):11424–11430.

McDonald et al., "A structural superfamily of growth factors containing a cystine knot motif" *Cell* (1993) 73:421–424.

Muesch et al., "A novel pathway for secretory proteins?" *TIBS 15* (Mar. 1990) pp. 86–88.

Peek et al., "Characterization of a periplasmic thiol:disulfide interchange protein required for the functional maturation of secreted virulence factors of *Vibrio cholerae*" *Proc. Natl. Acad. Sc. USA* (1992) 89:6210–6214.

Priestle et al., "Crystallographic refinement of interleukin 1β at 2.0 Å resolution" *Proc. Natl. Acad. Sci. USA* (1989) 86:9667–9671.

Rubartelli et al., "A novel secretory pathway for interleukin–1β, a protein lacking a signal sequence" *Embo J.* (1990) 9(5):1503–1510.

Rubartelli et al., "Secretion of thioredoxin by normal and neoplastic cells through a leaderless secretory pathway" *J. Biol. Chem.* (1992) 267(34):24161–24164.

Singer et al., "Interleukin 1β is localized in the cytoplasmic ground substance but is largely absent from the golgi apparatus and plasma membranes of stimulated human monocytes" *J. Exp. Med.* (1988) 167:389–407.

Studier et al., "Use of bacteriophage T7 RNA polymerase to direct selective high–level expression of cloned genes" *J. Mol. Biol.* (1986) 189:113–130.

Squires et al., Production and characterization of human basic fibroblast growth factor from *Escherichia coli J. Biol. Chem.* (1988) 263(31):16297–16302.

Sutcliffe, "Nucleotide sequence of the ampicillin resistance gene of *Escherichia coli* plasmid pBR322" *Proc. Natl. Acad. Sci. USA* (1978) 75(8):3737–3741.

von Heijne, "A new method for predicting signal sequence cleavage sites" *Nucleic Acids Res.* (1986) 14(11):4683–4690.

Young et al., "Modularity of protein function: chimeric interleukin 1βs containing specific protease inhibitor loops retain function of both molecules" *Biochem.* (1993) 32:5327–5331.

Zhang et al., "Three–dimensional structure of human basic fibroblast growth factor, a structural homolog of interleukin 1β" *Proc. Natl. Acad. Sci. USA* (1991) 88:3446–3450.

Zhu et al., "Three–dimensional structures of acidic and basic fibroblast growth factors" *Science* (1991) 251:90–94.

MacDougall et al., "Cloning and expression of protease genes from *Treponema denticola* in *Escherichia coli*" *Oral Microbiol. Immunol.* (1991) 6:270–274.

Madden et al., "Expression of *Porphyromonas gingivalis* proteolytic activity in *Escherichia coli*" *Oral Microbiol. Immunol.* (1992) 7:349–356.

Sedláček et al., "Processed enzymatically active protease ($p15^{gag}$) of avial retrovirus obtained in an *E. coli* system expressing a recombinant precursor ($Pr25^{lac-\Delta gag}$)" *FEBS Lett.* (1988) 237:187–190.

Garcia et al., "Artificial cleavage site recognized by plum pox potyvirus protease in *Escherichia coli*" *J. Virol.* (1989) 63:2457–2460.

Knott et al., "The expression and purification of human rhinovirus protease 3C" *Eur. J. Biochem.* (1989) 182:547–555.

Aschauer et al., "Biologically active protease 3C of human rhinovirus 1A is expressed from a cloned cDNA segment in *Escherichia coli*" *Virol.* (1991) 184:587–594.

Torruella et al., "Cauliflower mosaic virus produces an aspartic proteinase to cleave its polyproteins" *EMBO J.* (1989) 8:2819–2825.

Danley et al., "Crystallizable HIV–1 protease derived from expression of the viral pol gene in *Escherichia coli*" *Biochem. Biophys. Res. Commun.* (1989) 165:1043–1050.

Grundmann et al., "Cloning and expression of a cDNA encoding human placental protein 11, a putative serine protease with diagnostic significance as a tumor marker" *DNA and Cell Biol.* (1990) 9:243–250.

Pamer et al., "Expression and deletion analysis of the *Trypanosoma brucei rhodesiense* cysteine protease in *Escherichia coli*" *Infect. Immun.* (1991) 59:1074–1078.

Arnott et al., "Cloning and expression of a *porphyromonas (bacteroides) gingivalis* protease gene in *Escherichia coli*" *Archs. Oral Biol.* (1990) 35:97S–99S.

Windheuser et al., "Expression of functional beta–galactosidase containing the coxsackievirus 3C protease as an internal fusion" *Biochem. Biophys. Res. Comm.* (1991) 177:243–251.

Shapira et al., "Gene expression by a hypovirulence–associated virus of the chestnut blight fungus involves two papain–like protease activities" *J. Biol. Chem.* (1991) 266:19419–19425.

Hayakawa et al., "Expression of human T–cell leukemia virus type I protease in *Escherichia coli*" *Biochem. Biophys. Res. Comm.* (1991) 181:1281–1287.

Bourgeau et al., "Cloning, expression and sequencing of a protease gene (tpr) from *Porphyromonas gingivalis* W83 in *Escherichia coli*" *Infect. Immun.* (1992) 60:3186–3192.

Menéndez–Arias et al., "Purification and characterization of the mouse mammary tumor virus protease expressed in *Escherichia coli*" *J. Biol. Chem.* (1992) 267:24134–24139.

Baum et al., "Expression and analysis of the human cytomegalovirus UL80–encoded protease: Identification of autoproteolytic sites" *J. Virol.* (1993) 67:497–506.

Saiga et al., "Human T–cell leukemia virus type 1 protease protein expressed in *Escherichia coli* possesses aspartic proteinase activity" *Arch. Virol.* (1993) 128:195–210.

Eakin et al., "Production of crystallizable cruzain, the major cysteine protease from *Trypanosoma cruzi*" *J. Biol. Chem.* (1993) 268:6115–6118.

Dargatz et al., "The heterodimeric protease clostripain from *Clostridium histolyticum* is encoded by a single gene" *Mol. Gene Genet.* (1993) 240:140–145.

Weinheimer et al., "Autoproteolysis of herpes simplex virus type I protease releases an active catalytic domain found in intermediate capsid particles" *J. Virol.* (1993) 67:5813–5822.

Gill et al., "*Myxococcus xanthus* encodes an ATP–dependent protease which is required for developmental gene transcription and intercellular signaling" *J. Bacteriol.* (1993) 175:4538–4544.

Walker et al., "Efficient and rapid affinity purification of proteins using recombinant fusion proteases" *Bio/Technology* (1994) 12:601–605.

Loeb et al., "Mutational analysis of human immunodeficiency virus Type 1 protease suggests functional homology with aspartic proteinases" *J. Virol.* (1989) 63:111–121.

Alignment of IL1-like protein sequences

```
(1) dsbA: (19) AQYEDGK---QYTTLE---KP-VAGAP FEE-VL
(2) IL1b:      APVR----SLNCTLRDSQQKSLVMSGP YELKAL
(3) IL1a:      APF-SFLSNVKYNFMRIIKYEFILNDA IRANDQ
(4) FGFb: (14) GHFKDPK-RLYC-KNGG--F-FLRIHP -DGRV-
(5) FGFa: ( 5) GNYKKPK-LLYCS-NGG--Y-FLRILP -DGTV- (1)     HISDNVKKKLPEGVKMTKYHVNF-MGGDL-GKDLTQAWAVAM-
(2)     HLQ---------GQDM-EQQVVFSMSF-VQGEESNDKIPVAL-
(3)     YLTAAAL------HNL-DEAVKFDMGA-YKSSKDDAKITVIL-
(4)     ---DGVREK-------SDPHIKLQ----LQAEE---RGVVSIK
(5)     ---DGTKDR-------SDQHIQLQ----LCAESI---GEVYIK (1)     AL-----------GVEDKVTVPLFEGV--QKTQTIRSASDIRDVF
(2)     GLKEKNLYLSCVLKDDKPTLQL-ESVD-PKNYPKKKM-EKRFVF
(3)     RISKTQLYVTAQD-EDQPVLLK-EMPEIPKTIT--GS-ETNLLF
(4)     GV-CANRYL--AMKED---GRLLAS---------KCVTDECFFF
(5)     ST-ETGQFL--AMDTD---GLLYGS------QTP---NEECLFL (1)     INAG1--KGEEYDAA KYQLNPQGMDTS---NMDVF-V------
(2)     NKIEINNKL-EFESA --QFPNWYISTSQAENMPVF-LGGTKGG
(3)     FWETHGTKN-YFTSV --AHPNLFIATKQ--DYWVC-L--AGGP
(4)     ERLESNNYN-TYRSR KY--TSWYVALKRTGQ---YKLGSKTGP
(5)     ERLEENHYN-TYISK KHAEKHWFVGLKKNGR---SKLGPRTHF (1)     QQYAD-TVKYL--SEKK
(2)     QDITDFTMQFV----SS
(3)     PSITDFQILEN----QA
(4)     GQKA---ILFLPMSAKS
(5)     GQKA---ILFLPLPVSS
```

FIGURE 1

Homology between members of the IL1-like protein family

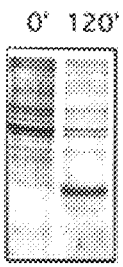  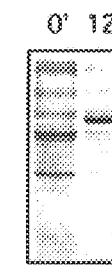 
FIG. 7A   FIG. 7B   FIG. 7C   FIG. 7D
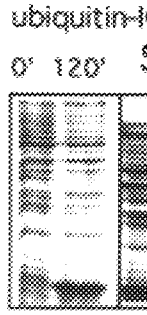 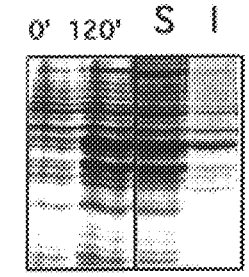 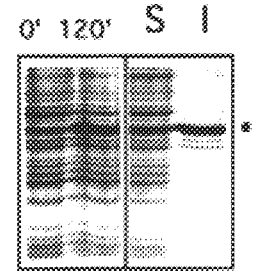 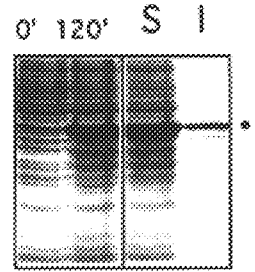
FIG. 8A   FIG. 8B   FIG. 8C   FIG. 8D

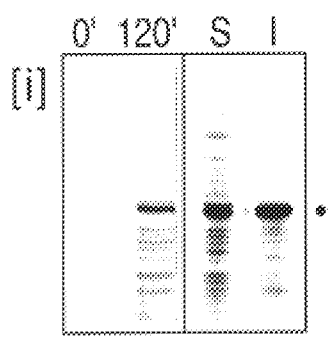
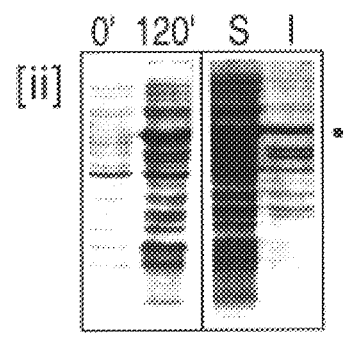
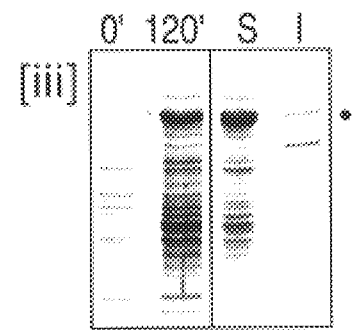
FIG. 9A  FIG. 9B  FIG. 9C
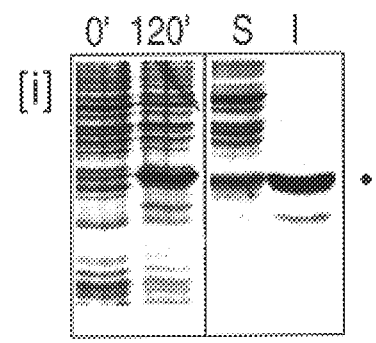
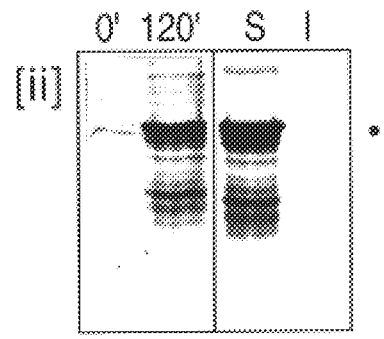
FIG. 10A  FIG. 10B

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 142 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Ala  Gln  Tyr  Glu  Asp  Gly  Lys  Gln  Tyr  Thr  Thr  Leu  Glu  Lys  Pro  Val
  1                   5                            10                          15

Ala  Gly  Ala  Pro  Phe  Glu  Glu  Val  Leu  His  Ile  Ser  Asp  Asn  Val  Lys
                 20                           25                          30
```

| | | | | | | | | | | | | | | |
|---|---|---|---|---|---|---|---|---|---|---|---|---|---|---|
|Lys|Lys|Leu 35|Pro|Glu|Gly|Val|Lys 40|Met|Thr|Lys|Tyr|His 45|Val|Asn|Phe|
|Met|Gly 50|Gly|Asp|Leu|Gly|Lys 55|Asp|Leu|Thr|Gln|Ala 60|Trp|Ala|Val|Ala|
|Met 65|Ala|Leu|Gly|Val|Glu 70|Asp|Lys|Val|Thr|Val 75|Pro|Leu|Phe|Glu|Gly 80|
|Val|Gln|Lys|Thr|Gln 85|Thr|Ile|Arg|Ser|Ala 90|Ser|Asp|Ile|Arg|Asp 95|Val|
|Phe|Ile|Asn|Ala 100|Gly|Ile|Lys|Gly|Glu 105|Glu|Tyr|Asp|Ala|Ala 110|Lys|Tyr|
|Gln|Leu|Asn 115|Pro|Gln|Gly|Met|Asp 120|Thr|Ser|Asn|Met|Asp 125|Val|Phe|Val|
|Gln|Gln 130|Tyr|Ala|Asp|Thr|Val 135|Lys|Tyr|Leu|Ser|Glu 140|Lys|Lys|

( 2 ) INFORMATION FOR SEQ ID NO:2:

( i ) SEQUENCE CHARACTERISTICS:
        ( A ) LENGTH: 153 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

| | | | | | | | | | | | | | | | |
|---|---|---|---|---|---|---|---|---|---|---|---|---|---|---|---|
|Ala 1|Pro|Val|Arg|Ser 5|Leu|Asn|Cys|Thr|Leu 10|Arg|Asp|Ser|Gln|Gln 15|Lys|
|Ser|Leu|Val|Met 20|Ser|Gly|Pro|Tyr|Glu 25|Leu|Lys|Ala|Leu|His 30|Leu|Gln|
|Gly|Gln|Asp 35|Met|Glu|Gln|Gln|Val 40|Val|Phe|Ser|Met|Ser 45|Phe|Val|Gln|
|Gly|Glu 50|Glu|Ser|Asn|Asp|Lys 55|Ile|Pro|Val|Ala|Leu 60|Gly|Leu|Lys|Glu|
|Lys 65|Asn|Leu|Tyr|Leu|Ser 70|Cys|Val|Leu|Lys|Asp 75|Asp|Lys|Pro|Thr|Leu 80|
|Gln|Leu|Glu|Ser|Val 85|Asp|Pro|Lys|Asn|Tyr 90|Pro|Lys|Lys|Lys|Met 95|Glu|
|Lys|Arg|Phe|Val 100|Phe|Asn|Lys|Ile|Glu 105|Ile|Asn|Asn|Lys|Leu 110|Glu|Phe|
|Glu|Ser|Ala 115|Gln|Phe|Pro|Asn|Trp 120|Tyr|Ile|Ser|Thr|Ser 125|Gln|Ala|Glu|
|Asn|Met 130|Pro|Val|Phe|Leu|Gly 135|Gly|Thr|Lys|Gly|Gly 140|Gln|Asp|Ile|Thr|
|Asp 145|Phe|Thr|Met|Gln|Phe 150|Val|Ser|Ser|

( 2 ) INFORMATION FOR SEQ ID NO:3:

( i ) SEQUENCE CHARACTERISTICS:
        ( A ) LENGTH: 153 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

| | | | | | | | | | | | | | | | |
|---|---|---|---|---|---|---|---|---|---|---|---|---|---|---|---|
|Ala 1|Pro|Phe|Ser|Phe 5|Leu|Ser|Asn|Val|Lys 10|Tyr|Asn|Phe|Met|Arg 15|Ile|
|Ile|Lys|Tyr|Glu 20|Phe|Ile|Leu|Asn|Asp 25|Ala|Ile|Arg|Ala|Asn 30|Asp|Gln|

```
       Tyr  Leu  Thr  Ala  Ala  Ala  Leu  His  Asn  Leu  Asp  Glu  Ala  Val  Lys  Phe
                 35                      40                 45

Asp  Met  Gly  Ala  Tyr  Lys  Ser  Ser  Lys  Asp  Asp  Ala  Lys  Ile  Thr  Val
            50                      55                 60

Ile  Leu  Arg  Ile  Ser  Lys  Thr  Gln  Leu  Tyr  Val  Thr  Ala  Gln  Asp  Glu
       65                      70                      75                            80

Asp  Gln  Pro  Val  Leu  Leu  Lys  Glu  Met  Pro  Glu  Ile  Pro  Lys  Thr  Ile
                           85                      90                      95

Thr  Gly  Ser  Glu  Thr  Asn  Leu  Leu  Phe  Phe  Trp  Glu  Thr  His  Gly  Thr
                      100                     105                     110

Lys  Asn  Tyr  Phe  Thr  Ser  Val  Ala  His  Pro  Asn  Leu  Phe  Ile  Ala  Thr
                      115                     120                     125

Lys  Gln  Asp  Tyr  Trp  Val  Cys  Leu  Ala  Gly  Gly  Pro  Pro  Ser  Ile  Thr
                 130                     135                     140

Asp  Phe  Gln  Ile  Leu  Glu  Asn  Gln  Ala
       145                     150
```

( 2 ) INFORMATION FOR SEQ ID NO:4:

( i ) SEQUENCE CHARACTERISTICS:
        ( A ) LENGTH: 132 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
       Gly  His  Phe  Lys  Asp  Pro  Lys  Arg  Leu  Tyr  Cys  Lys  Asn  Gly  Gly  Phe
       1                       5                       10                      15

Phe  Leu  Arg  Ile  His  Pro  Asp  Gly  Arg  Val  Asp  Gly  Val  Arg  Glu  Lys
                      20                      25                      30

Ser  Asp  Pro  His  Ile  Lys  Leu  Gln  Leu  Gln  Ala  Glu  Glu  Arg  Gly  Val
                      35                      40                      45

Val  Ser  Ile  Lys  Gly  Val  Cys  Ala  Asn  Arg  Tyr  Leu  Ala  Met  Lys  Glu
            50                      55                      60

Asp  Gly  Arg  Leu  Leu  Ala  Ser  Lys  Cys  Val  Thr  Asp  Glu  Cys  Phe  Phe
       65                      70                      75                            80

Phe  Glu  Arg  Leu  Glu  Ser  Asn  Asn  Tyr  Asn  Thr  Tyr  Arg  Ser  Arg  Lys
                           85                      90                      95

Tyr  Thr  Ser  Trp  Tyr  Val  Ala  Leu  Lys  Arg  Thr  Gly  Gln  Tyr  Lys  Leu
                      100                     105                     110

Gly  Ser  Lys  Thr  Gly  Pro  Gly  Gln  Lys  Ala  Ile  Leu  Phe  Leu  Pro  Met
                      115                     120                     125

Ser  Ala  Lys  Ser
                 130
```

( 2 ) INFORMATION FOR SEQ ID NO:5:

( i ) SEQUENCE CHARACTERISTICS:
        ( A ) LENGTH: 134 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
       Gly  Asn  Tyr  Lys  Lys  Pro  Lys  Leu  Leu  Tyr  Cys  Ser  Asn  Gly  Gly  Tyr
       1                       5                       10                      15

Phe  Leu  Arg  Ile  Leu  Pro  Asp  Gly  Thr  Val  Asp  Gly  Thr  Lys  Asp  Arg
                      20                      25                      30

Ser  Asp  Gln  His  Ile  Gln  Leu  Gln  Leu  Cys  Ala  Glu  Ser  Ile  Gly  Glu
```

```
                              35                        40                              45
       Val  Tyr  Ile  Lys  Ser  Thr  Glu  Thr  Gly  Gln  Phe  Leu  Ala  Met  Asp  Thr
            50                        55                       60

Asp  Gly  Leu  Leu  Tyr  Ser  Gln  Thr  Pro  Asn  Glu  Glu  Cys  Leu  Phe
       65                        70                       75                        80

Leu  Glu  Arg  Leu  Glu  Glu  Asn  His  Tyr  Asn  Thr  Tyr  Ile  Ser  Lys  Lys
                      85                        90                            95

His  Ala  Glu  Lys  His  Trp  Phe  Val  Gly  Leu  Lys  Lys  Asn  Gly  Arg  Ser
                      100                      105                      110

Lys  Leu  Gly  Pro  Arg  Thr  His  Phe  Gly  Gln  Lys  Ala  Ile  Leu  Phe  Leu
                      115                      120                      125

Pro  Leu  Pro  Val  Ser  Ser
                      130
```

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
       Asp  Arg  Gly  Gly
       1
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
       His  His  His  His  His  His  Ser
       1                   5
```

( 2 ) INFORMATION FOR SEQ ID NO:8:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
GGATCCCGTG   GAGGATTAAA   CCATGGATGC   ATAAGCTTCG   AATTCTGCCA   GGCATGCAAG         60

CTCAGATCC                                                                          69
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
       Gly  Pro  Glu  Thr  Leu  Xaa  Gly  Ala  Glu  Leu
       1                   5                        10
```

( 2 ) INFORMATION FOR SEQ ID NO:10:

```
( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

Gly  Pro  Glu  Thr  Leu  Xaa  Gly  Ala
    1                    5

( 2 ) INFORMATION FOR SEQ ID NO:11:

( i ) SEQUENCE CHARACTERISTICS:
            ( A ) LENGTH: 12 amino acids
            ( B ) TYPE: amino acid
            ( C ) STRANDEDNESS: single
            ( D ) TOPOLOGY: linear ( x i ) SEQUENCE DESCRIPTION: SEQ ID NO:11:

Asp  Arg  Gly  Asp  Pro  His  His  His  His  His  His  Glu
    1                    5                        10

( 2 ) INFORMATION FOR SEQ ID NO:12:

( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: linear ( x i ) SEQUENCE DESCRIPTION: SEQ ID NO:12:

Asp  Pro  His  His  His  His  His  His  Glu
    1                    5
```

POLYPEPTIDE FUSIONS TO POLYPEPTIDES OF THE BETA-TREFOIL FOLD STRUCTURAL FAMILY

This application is a continuation of application Ser. No. 08/100,744, filed Aug. 2, 1993, U.S. Pat. No. 5,563,046.

TECHNICAL FIELD

The invention relates to the field of recombinant synthesis of proteins. In particular, polypeptides of interest are expressed as fusions to interleukin-1-like polypeptides.

BACKGROUND ART

Genetic engineering has made it possible to produce large amounts of polypeptides encoded by cloned DNA by means of recombinant expression systems, especially by expression in such prokaryotes as *Escherichia coli*. The expressed heterologous polypeptide, which would otherwise either not be produced at all by the host cell or be produced only in limited amounts, may constitute a significant proportion of the total cellular polypeptide of the host cell.

Several problems are frequently encountered, however. Polypeptides over-expressed in the bacterial cytoplasm often accumulate as insoluble "inclusion bodies" (Williams et al., *Science* 215:687–688, 1982; Schoner et al., *Biotechnology* 3:151–154, 1985). Inclusion body formation is not limited to bacterial expression systems. For example, the Kruppel gene product of *Drosophila* can form inclusion bodies when produced in insect cells using a baculovirus expression system. Polypeptides accumulated in the form of inclusion bodies are relatively useless for screening purposes in biological or biochemical assays. Conversion of this insoluble material into active, soluble polypeptide requires slow and difficult solubilization and refolding protocols which often greatly reduce the net yield of biologically active polypeptide.

Even when heterologous polypeptides are expressed in the cytoplasm of bacteria in soluble form, they often accumulate poorly as a result of degradation by host proteases. Further, the accumulated polypeptides often have a different amino terminus than that which is desired.

One approach to these problems is to fuse a polypeptide of interest to a polypeptide fusion partner such as the lacZ and trpE gene products (Goeddel et al., *Proc. Natl. Acad. Sci. U.S.A.* 76:106–110, 1979; Furman et al. *Biotechnology* 5:1047–1051, 1987); maltose-binding polypeptide (Di Guan et al., *Gene* 67:21–30, 1988); glutathione-S-transferase (Johnson, *Nature* 338:585–587, 1989); ubiquitin (Miller et al., *Biotechnology* 7:698–704, 1989); or thioredoxin (LaVallie et al.,*Biotechnology* 11:187–193, 1993). Often the fusion partner confers such desirable characteristics as greater solubility on the polypeptide of interest, especially when the recombinant host is cultured at temperatures below the optimum for growth (LaVallie et al., 1993, op. cit.). Low-temperature culture, however, introduces other practical problems which may make the process less suitable on a commercial scale.

The use of polypeptide fusions also allows the production of polypeptides which might otherwise be too small to accumulate efficiently in the recombinant host (Schultz et al.,*J. Bacteriol.* 169:5385–5392, 1987). Further, appropriate fusion partners may act, e.g., as affinity peptides, facilitating recovery and purification of the fusion polypeptide from cell extracts containing hundreds of other polypeptides (see, e.g., WO 91/11454).

The use of fusion polypeptides has drawbacks, however. It is often necessary to cleave the desired polypeptide away from the fusion partner by enzymatic or chemical means. This can be accomplished by placing an appropriate target sequence for cleavage between that for the fusion partner and for the desired polypeptide. Unfortunately, the enzymes most widely used for polypeptide cleavage are expensive, inefficient, or imprecise in their cleavage, and cannot always be successfully applied to a majority of fusion constructs. For example, enterokinase and Factor Xa are mammalian enzymes which are expensive to produce and require that a polypeptide of interest expressed in a prokaryotic host cell be isolated from the host cell before being treated with the mammalian enzyme, adding considerable expense to a large-scale process. Further, the efficiency with which these enzymes cleave substrates is highly variable. While an enzyme like subtilisin, for example, may be relatively inexpensive to produce, the precision with which it cleaves substrates is less than acceptable for commercial-scale processes under current "Good Manufacturing Practices" (GMP).

Some yeast ubiquitin hydrolases efficiently cleave fusions in which ubiquitin is the fusion partner and the amino acid immediately downstream of the cleavage site is not proline (Miller et al., op. cit., 1989; Tobias and Varshavsky, *J. Biol. Chem.* 266:12021–12028, 1991; see also WO 88/02406 and WO 89/09829). One ubiquitin hydrolase gene cloned from the yeast *Saccharomyces cerevisiae*, YUH-1 (Miller et al., op. cit. 1989), will not efficiently cleave fusions in which the downstream polypeptide is larger than about 25 kD. Another *S. cerevisiae* ubiquitin hydrolase gene (Tobias and Varshavsky, *J. Biol. Chem.* 266:12021–12028, 1991) is capable of cleaving ubiquitin fusions in which the polypeptide downstream of the cleavage site is as large as 130 kD. Both ubiquitin hydrolases are active when expressed intracellularly in *E. coli*, allowing them to be used to cleave fusions in vivo. However, the use of ubiquitin as a fusion partner is hampered by the fact that multi-copy plasmids carrying ubiquitin fusion constructs may cause *E. coli* host cells, for example, to grow slowly and lose viability.

Cytoplasmic accumulation of fusion polypeptides suffers from the drawback that the heterologous polypeptide moiety may not be able to fold correctly in the strong reducing environment of the cytoplasm, leading to poor yields of biologically active polypeptide. To overcome this problem the polypeptide of interest may be fused to "signal peptides," short (15–30 amino acid) sequences present at the amino terminus of precursor polypeptides destined for secretion, i.e. export to non-cytoplasmic locations. In *E. coli* such locations would include the inner membrane, periplasmic space, cell wall and outer membrane. Typically, at some point just prior to or during transport of polypeptides out of the cytoplasm, the signal sequence is removed by host enzymes to produce the "mature" polypeptide. (For a recent review of the general secretory pathway in gram-negative bacteria and a discussion of signal peptides, see Pugsley, *Microbiol. Rev.* 57:50–108, 1993).

Localization of an expressed polypeptide to the periplasmic space is advantageous because simpler methods of polypeptide recovery can be used, including "osmotic shock" and other techniques. Although signal sequences may be used to deliver heterologous polypeptides into the periplasmic space of *E. coli*, few polypeptides are efficiently accumulated in soluble form by this method. Translocation of polypeptides across the lipid bilayer of the inner membrane appears to be inefficient, particularly in the case of fusions to heterologous polypeptides. Only a few polypeptides lacking a signal sequence have been reported to be selectively released from cells by osmotic shock, freezethaw and other treatments. These include thioredoxin (Lunn and Pigiet, op. cit., 1982) and elongation factor-Tu (EF-Tu) (Jacobson et al., *Biochemistry* 15:2297–2302, 1976). IL-1-β expressed in *E. coli* has been extracted by a modified osmotic shock procedure (Joseph-Liauzun et al., op. cit., 1990).

Extracellular localization may also be advantageous and may be accomplished by at least two different strategies: (1) Permeabilization of the outer membrane, allowing periplasmic polypeptides to "leak" out (U.S. Pat. No. 4,595,658; Kato et al., *Gene* 54:197–202, 1987); and (2) fusion to sequences which direct extracellular export (Nagahari et al., *EMBO J.* 4:3589–3592, 1985; U.S. Pat. No. 5,143,830). However, these methods do not work in many cases; and even if they do work, the methods generally are inefficient and often do not produce polypeptides with the desired amino terminus (Holland et al., *Biochimie* 72:131–141, 1990).

The ideal fusion partner would be one which is useful for the production of a wide variety of heterologous polypeptides in a recombinant host cell, e.g., *E. coli,* at optimum growth temperatures. Preferably, such a fusion partner would improve the accumulation of the desired polypeptide in soluble, active form in a cellular location in which it is protected, e.g., from proteolysis, and where the fusion polypeptide may be recovered by simplified procedures. It would also be advantageous if such a fusion partner would allow the use of an efficient, inexpensive and precise cleavage system in vivo.

DISCLOSURE OF INVENTION

The present invention is directed to fusion polypeptides comprising an interleukin-1-like ("IL-1-like) polypeptide, such as IL-1-β, mature IL-1 receptor antagonist, or mature *E. coli* DsbA, and a polypeptide of interest. When fused to IL-1-like polypeptides, polypeptides may be produced in a wide variety of host cells, e.g., *E. coli* in soluble, active, and easily recoverable form at temperatures at or close to the physiological optima for host cell growth. Preferably, between the IL-1-like polypeptide and the polypeptide of interest is a linker peptide. The linker peptide which may serve a variety of functions, e.g., providing a polypeptide cleavage site, preferably is one cleaved by ubiquitin hydrolase. A variety of polypeptides of interest may be produced in this manner, including enzymes, growth factors, antibodies, DNA- or RNA-binding proteins, and membrane receptors.

Also provided are nucleic acids, preferably expression vectors, encoding such fusion polypeptides and host cells comprising such nucleic acids. Preferably, such host cells additionally comprise a nucleic acid capable of expressing in the cytoplasm of the host cell a proteolytic enzyme which specifically recognizes a proteolytic enzyme cleavage site in the fusion polypeptide, preferably in the linker. Such a system is useful for in vivo cleavage of the fusion polypeptides, particularly when ubiquitin hydrolase is co-expressed and cleaves the fusion polypeptide at a site located within a linker positioned between the IL-1-like polypeptide and the polypeptide of interest.

These transformed host cells are useful for the recombinant production of polypeptides of interest as fusions to an IL-1-like polypeptide, again, preferably using in vivo cleavage to cleave away from the polypeptide of interest other sequences of the fusion polypeptide, e.g., the IL-1-like polypeptide and linker (if present).

BRIEF DESCRIPTION OF DRAWINGS

FIG. 1 (SEQ ID NO:2, SEQ ID NO:3, SEQ ID NO:4, and SEQ ID NO:5) shows an alignment of the sequences of five members of the IL-1-like protein family: (1) *E. coli* DsbA (SEQ ID NO:1), (2) human IL-1-β (SEQ ID NO:2), (3) human IL-1-α (SEQ ID NO:3), (4) human basic fibroblast growth factor (FGF) (SEQ ID NO:4), and (5) human acidic FGF (SEQ ID NO:5).

FIG. 7, left, shows SDS-PAGE gels of WCL, 0' and 120', and soluble ("S") and insoluble ("I") fractions from *E. coli* cells transformed with pDJ16920, which encodes ubiquitin-TGF-β2 fusion polypeptide, expected size approximately 20 kD, or plasmid pYZ22096, which encodes a DsbA-ubiquitin-TGF-β2 fusion, expected size approximately 42 kD.

FIG. 8, left: SDS-PAGE gels of WCL, 0' and 120' and soluble ("S") and insoluble ("I") fractions from *E. coli* cells transformed with pDJ16927, which expresses a ubiquitin-IGF fusion, expected size of about 15 kD, or with pDM16965, which expresses IL-1-β-ubiguitin-IGF, expected size approximately 32 kD. FIG. 8, right shows similar gels of extracts of *E. coli* cells transformed with pYZ22070, which encodes DsbA-ubiquitin-IGF, with an expected size of approximately 37 kD, or with pDM15426, which encodes DsbA-ubiquitin-IGF in which DsbA has its native signal sequence, expected size of about 37 kD.

FIG. 9 shows SDS-PAGE gels of fractions of *E. coli* cells expressing fusions to IGFBP-3. Panel [i]: WCL at 0' and 120' and "soluble" ("S") and "insoluble" ("I") extracts of *E. coli* cells expressing pDJ12875, which encodes a ubiquitin-IGFBP-3 fusion having an expected size approximately 38 kD; panel [ii], IL-1-ubiquitin-IGFBP-3 having an expected size of approximately 55 kD (pDM16967); and [iii], DsbA-ubiquitin-IGFBP-3 having an expected size of approximately 60 kD (pDM15427).

FIG. 10, panel [i], shows SDS-PAGE gels of WCL at 0' and 120' and "soluble" ("S") and "insoluble" ("I") fractions from *E. coli* cells expressing a ubiquitin-TGF-βR fusion with an expected size of approximately 24 kD (pDJ16921); panel [ii], a DsbA-ubiquitin-TGF-βR fusion with an expected size of approximately 46 kD (pDM15428).

FIGS. 11A and B: HPLC-reverse phase elution profiles from ubiquitin hydrolase-cleaved IGF-I derived from cultures of DsbA-ubiquitin-IGF and ubiquitin-IGF constructs, respectively, grown at 30° C. C and D: ubiquitin hydrolase-cleaved DsbA-ubiquitin-IGF and ubiquitin-IGF, respectively, grown at 37° C. The specific activity of the IGF peaks is shown as boxed values, arbitrary units).

Figure 12:
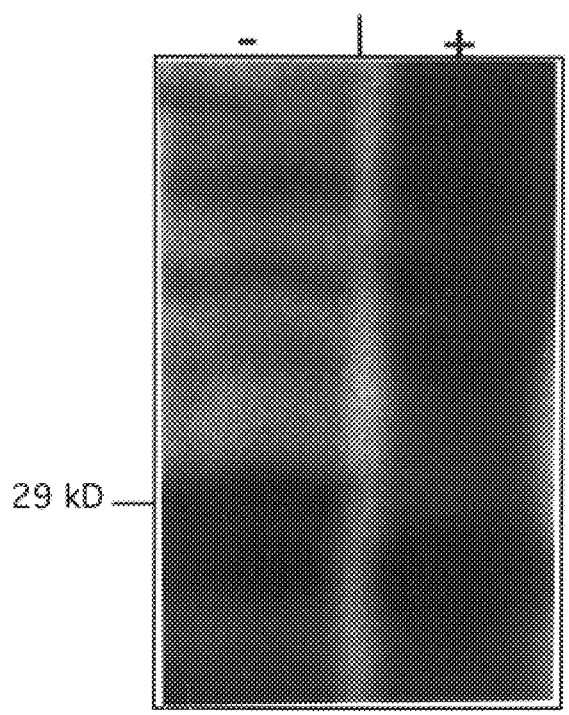

FIG. 12 shows SDS-PAGE gels of partially purified TGF-βR (136 amino acid extracellular domain, pDM15428) cross-linked with $^{125}$I-radiolabeled TGF-β1. The size of the expected cross-linked product is approximately 30 kD. Left (−): no added cold TGF-β1. Right (+): excess cold TGF-β1 (2500-fold molar).

Figures 13A, 13B:
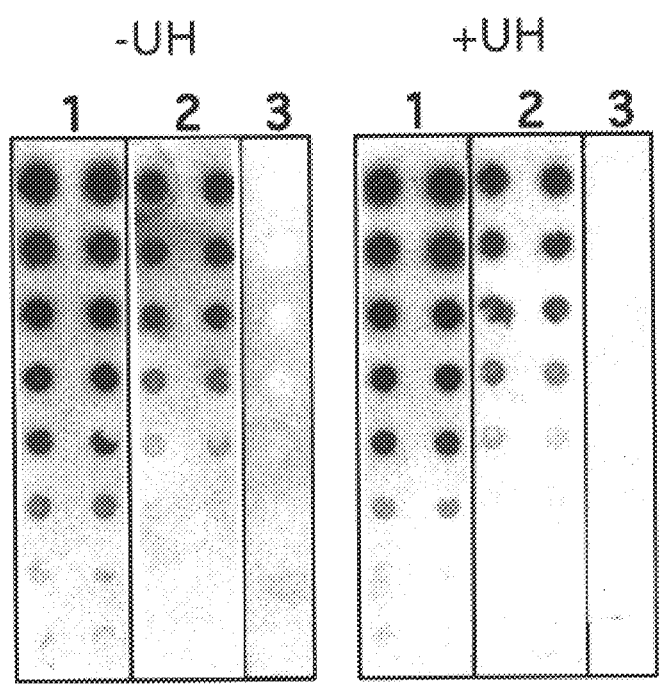

FIG. 13 shows results of dot-blot assays using $^{125}$I-radiolabeled IGF-I to measure binding activity in crude extracts ("soluble" fraction) of *E. coli* cells expressing (1) pDM15427, which encodes a DsbA-ubiquitin-IGFBP-3 fusion; (2) pDJ12875, which encodes a ubiquitin-IGFBP-3 fusion; or (3) pDJ12887, a "vector only" control. Samples were untreated (−UH) or cleaved with ubiquitin hydrolase (+UH).

Figure 14:
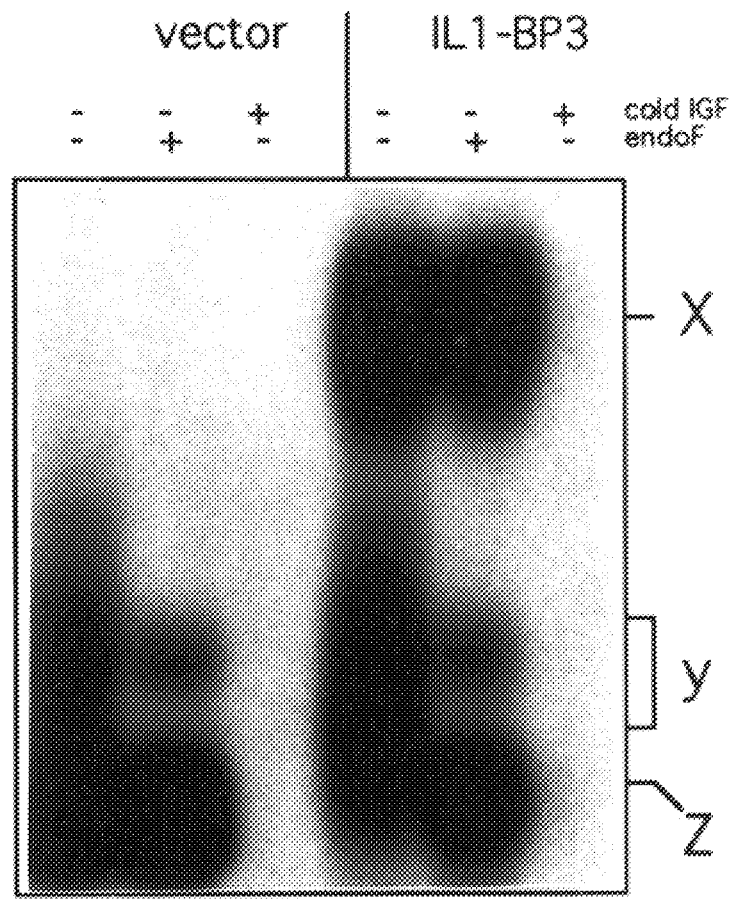

FIG. 14 shows SDS-PAGE gels of cross-linked samples from COS cells transiently transfected pDM15430, which encodes IL-1-β-IGFBP-3 ("IL1-BP3") or the vector alone ("vector"), with (+) or without (−) treatment of the crosslinked sample with endoglycosidase F, and with or without competition with "cold" IGF. On the right side of the figure are labels for the 55 kD fusion polypeptide (X), a native, glycosylated IGF binding protein (Y) and the native, deglycosylated IGF binding protein (Z).

MODES FOR CARRYING OUT THE INVENTION

A wide range of polypeptides, when fused to an interleukin-1-like polypeptide ("IL-1-like polypeptide"), accumulate in large quantities in soluble, active, easily recoverable form in a variety of host cells at temperatures close to or at the physiological optima for host cell growth. If desired, the polypeptide of interest may be cleaved away from the interleukin-1-like polypeptide efficiently and inexpensively either in vivo or in vitro. Interleukin-1-β and related polypeptides are useful as generic fusion partners for the expression of a wide variety of heterologous polypeptides in both prokaryotic and eukaryotic cells, including *E. coli,* yeast, and mammalian cells.

Interleukin-1-β (IL-1-β) is one of a unique class of naturally secreted polypeptides which lack signal sequences (Muesch et al., *TIBS,* March 1990, pp. 86–88, 1990). Members of this class may be found in a wide range of species, from bacteria to humans. In mammalian monocytes IL-1-β secretion has been shown to be independent of the general secretory pathway (Rubartelli et al., *EMBO J.* 9:1503–1510, 1990; Singer et al., *J. Exp. Med.* 167:389–407, 1988; see also Rubartelli et al., *J. Biol. Chem.* 267:24161–24164, 1992).

Although IL-1-β does not contain an amino-terminal signal peptide or a significant hydrophobic region which could function as an internal signal sequence, when the gene for IL-1-β is expressed in *E. coli* host cells, the IL-1-β polypeptide can be released from the host cells by osmotic shock without lysing the cells (Joseph-Liauzun et al., *Gene* 86:291–295, 1990). Moreover, IL-1-β containing an amino-terminal methionine (Met-IL-1-β) is secreted by yeast cells (G. P. Livi, personal communication, reported in Joseph-Liauzun et al., op. cit., 1990).

It is believed that in mammalian monocytes IL-1 interacts with the cytoplasmic membrane, forms vesicles and is secreted without passing through the endoplasmic reticulum (ER) or Golgi apparatus. Because of this property, consensus glycosylation sites on the polypeptide remain unglycosylated. However, glycosylation of IL-1-β does occur if a cleavable signal sequence is attached to its amino terminus (Baldari et al., *EMBO J.* 6:229–234, 1987). The use of IL-1-like polypeptides as fusion partners can therefore permit production of nonglycosylated polypeptides in mammalian cells. This feature will be especially important in cases in which the glycosylation of a polypeptide of interest would be undesirable. For example, when human proteins are synthesized in other mammalian cells, different glycosylation may occur and may be antigenic to human recipients. This is a major area of concern for those interested in expressing polypeptides useful as human therapeutics in such transgenic animals as goats or sheep.

Moreover, since the alternative route of secretion employed by IL-1-like polypeptides avoids the ER, it may be advantageous to express polypeptides with free sulfhydryl groups, e.g., bFGF, PD-ECGF, and ADF (Takahashi et al., *Proc. Natl. Acad. Sci. U.S.A.* 83:8019–8023, 1986), as fusions to IL-1-like polypeptides because IL-1-like fusions avoid the oxidizing milieu of the ER lumen.

Also, IL-1-like fusions appear to be secreted without translocation across a lipid bilayer. Thus, using IL-1-like fusions with heterologous polypeptides which cannot normally be secreted via the general secretory pathway now permits the successful secretion of those polypeptides. Examples include but are not limited to polypeptides containing long hydrophobic or other sequences which can interfere with passage through the lipid bilayer.

For the purposes of the present invention, an "interleukin-1-like" (or "IL-1-like") polypeptide (or protein) is a polypeptide or functional fragment thereof characterized by a three-dimensional structure substantially similar to that of mature human interleukin-1-β (Priestle et al., *Proc. Natl. Acad. Sci. U.S.A.* 86:9667–9671, 1989). When fused to a polypeptide of interest, such an IL-1-like polypeptide is also capable of directing the secretion of that fusion polypeptide into a privileged cellular compartment in which the fusion polypeptide is soluble and biologically active but is protected from proteolysis.

In nature, mature IL-1-β is relatively small (about 17 kD) and stable. It is synthesized as a large inactive precursor which is later cleaved to release a mature polypeptide 153 amino acids long. Mature IL-1-β possesses a uniquely stable structure—a so-called beta-trefoil fold—characterized by three similar units arranged around a three-fold axis of symmetry to form a barrel structure, each unit containing two pairs of antiparallel beta strands. (Priestle et al., op. cit., 1989). This beta-trefoil fold, a structure which contains no alpha helices, may serve to stabilize the overall structure of a fusion polypeptide of which it is a part. Members of the beta-trefoil structural family include but are not limited to the following: IL-1-α and IL-1-β; members of the fibroblast growth factor (FGF) family including, e.g., acidic FGF and basic FGF, int-2, hst/KS3, FGF-5, FGF-6, and keratinocyte growth factor (zhang et al., *Proc. Natl. Acad. Sci. U.S.A.* 88:3446–3450, 1991; Zhu et al., *Science* 251:90–93, 1991); hisactophilin (Habazettl et al., *Nature* 359:855–857, 1992); and soybean trypsin inhibitor (Wolfson et al., *Biochemistry* 32:5327–5331, 1993). See also McDonald and Hendrickson, *Cell* 73:421–424, 1993.

Polypeptides which share the beta-trefoil structure will be considered IL-1-like polypeptides if, like IL-1, they are capable of directing the secretion of a fused polypeptide of interest into a privileged cellular compartment from which it can readily be released in active form, e.g., by a selective extraction procedure. For example, basic FGF, which lacks a signal sequence, is known to be secreted from cells by a process similar to that for IL-1-β (Abraham et al., *Science* 233:545–548, 1986).

IL-1-like polypeptides which have a beta-trefoil structure and are secreted from cells by a process similar to that for IL-1 may have evolved from a common ancestor to the point at which they no longer share any significant overall sequence homology (<20%) but retain key structural features. This could happen if residues critical to the structure do not change or are conservatively replaced. For example, FGF and IL-1-β are structurally similar but have weak sequence similarity. There is strong conservation in the hydrophobic character of residues at nine positions which form the hydrophobic core of the molecule and are situated around the internal three-fold axis (Zhu et al., op. cit., 1991).

"IL-1-like polypeptides" include polypeptides (a) which, when mature, lack an amino-terminal signal sequence recognizable by the method of von Heijne (*Nucl. Acids. Res.* 14:4683–4690, 1986), and (b) whose amino acid sequence is at least 20% homologous with the amino acid sequence of mature human interleukin-1-β (IL-1-β) when optimally aligned. Where an IL-1-like polypeptide is naturally synthesized as a precursor with an amino-terminal signal sequence, only the DNA sequence corresponding to the mature polypeptide, i.e., lacking a signal sequence, is considered the nucleic acid encoding the "IL-1-like polypeptide" for the purposes of the present invention. Again, a polypeptide possessing such characteristics is considered an "IL-1-like polypeptide" if it is capable of directing the secretion of a fused polypeptide of interest into a privileged cellular compartment.

Thus, the "IL-1-like polypeptides" of the present invention include the members of the interleukin-1 gene family, which includes interleukin-1-α and -β and the interleukin-1 receptor antagonist (IL-1ra) from human and nonhuman species (e.g., mouse and rat) (Eisenberg et al., *Nature* 343:341–346,. 1990; Eisenberg et al., *Proc. Natl. Acad. Sci. U.S.A.* 88:5232–5236, 1991).

The mature *E. coli* DsbA polypeptide (Bardwell et al., *Cell* 67:581–589, 1991; Kamitani et al., *EMBO J.* 11:57–62, 1992) and its known bacterial homologs (including *Vibrio cholerae* TcpG; Peek and Taylor, *Proc. Natl. Acad. Sci. U.S.A.* 89:6210–6214, 1992) are also examples of IL-1-like polypeptides by these criteria. DsbA is normally secreted to the periplasmic space, presumably with the aid of an amino-terminal signal sequence of 19 amino acids which is removed during translocation. However, a DsbA polypeptide in which the signal peptide is replaced by a single methionine displays unexpected behavior: Not only does the polypeptide cross the cell membrane, but transport across the membrane is actually increased. This indicates that DsbA transport does not involve the general secretory pathway. DsbA also can be released from cells by a modified osmotic shock procedure and other simplified methods which do not lyse the cell, as is shown in the Examples below.

FIG. 1 shows the sequence similarity between human IL-1-β DNA and the truncated dsbA gene. To maximize alignment, two regions of the dsbA sequence (corresponding to amino acid residues 21–35 and 126–157) are excluded from the comparison. The first of these segments (21–35) contains partial homology to active site regions of other oxidoreductases (Bardwell et al., op. cit., 1991). This region of homology is absent from the other classes of IL-1-like polypeptides, suggesting that this region is not necessary for the properties of the IL-1-like polypeptides of the present invention. The loop containing residues 21–35 may be removed (or replaced) without affecting polypeptide transport.

It should be noted that the term "interleukin" embraces a large number of proteins—26 to date—which vary widely in terms of sequence homology and structure. Interleukins other than IL-1 would generally not be considered "IL-1-like polypeptides" as defined above.

Thioredoxin is not considered an IL-1-like polypeptide. Thioredoxin secretion is similar in certain aspects to that of the IL-1-like polypeptides in that *E. coli* thioredoxin lacks a signal sequence and mammalian thioredoxin appears to be secreted without engaging the ER and Golgi apparatus. However, there is less than 15% sequence homology between IL-1 and thioredoxin, and there is no obvious similarity in their three-dimensional structures. Moreover, the secretion of IL-1-β differs from that of thioredoxin. For example, COS transfectants secrete thioredoxin but not IL-1-β. Moreover, in activated monocytes, some IL-1-β is found within intracellular vesicles, while the thioredoxin is not detected in membrane-bound compartments such as vesicles, suggesting that secreted thioredoxin molecules translocate directly to the plasma membrane (Rubartelli et al., op. cit., 1992). Thioredoxin preferentially resides at sites around the inner periphery of the cytoplasmic membrane in *E. coli* as adhesion zones, or Bayer's patches (sites at which there are gaps in the peptidoglycan cell wall where the inner and outer cell membranes are fused together). These observed differences in secretion between IL-1-β and thioredoxin indicate that these two polypeptides employ different secretory pathways.

LaVallie et al. (op. cit., 1993) have proposed the use of thioredoxin as a fusion partner, although some thioredoxin fusions become more soluble as the growth temperature of cells expressing them is lowered (LaVallie et al., op. cit., 1993).

Fusion polypeptides comprising the DNA sequence of an IL-1-like polypeptide fused to the DNA for a selected heterologous polypeptide, may be readily constructed by conventional genetic engineering techniques. The IL-1-like polypeptide is preferably fused to the amino terminus of the selected heterologous polypeptide, although fusion to the carboxy terminus of the selected polypeptide or insertion of the selected polypeptide into a site within an IL-1-like polypeptide may also be appropriate. For example, heterologous polypeptidase inhibitor loops have been inserted into IL-1-β at an internal site. See Wolfson et al., op. cit., 1993.

The nucleic acid encoding the fusion polypeptide may optionally contain, in addition to the IL-1-like polypeptide and the heterologous polypeptide of interest, additional "linker" DNA encoding additional amino acids.

A linker may serve a number of functions. First, a linker may provide a specific cleavage site between the IL-1-like polypeptide and the polypeptide of interest. Such a cleavage site may contain a target for a proteolytic enzyme such as, for example, Factor Xa, trypsin, collagenase, thrombin, or subtilisin enterokinase, or, preferably, ubiquitin hydrolase; or for such chemical cleavage agents as, for example, cyanogen bromide, or hydroxylamine.

A linker may also encode an "affinity tag" to aid in the purification of the fusion polypeptide away from other cellular polypeptides. For example, multiple histidine residues encoded by the linker allow the use of metal chelate affinity chromatography methods for purification of the fusion polypeptide.

The linker may also serve as a spacer, e.g., to prevent stearic hindrance in a fusion polypeptide between the IL-1-like polypeptide and the polypeptide of interest. Whether a linker is necessary will depend upon the structural and functional characteristics of the polypeptide of interest to be fused to an IL-1-like polypeptide, as will be apparent to those skilled in the art. If the polypeptide of interest is naturally cleaved, no linker may be necessary. The fusion polypeptide itself may be useful without cleavage.

The linker may serve any or all of these purposes or additional functions, or other functions as desired.

The ability of the IL-1-like polypeptide to target a fusion polypeptide to the extracellular space in the presence of other sequences within the same host cell (e.g., after permeabilization of the outer membrane, allowing periplasmic polypeptides to "leak" out, as taught in U.S. Pat. No. 4,595,658) simplifies the purification of the fusion polypeptide, since $E.$ $coli,$ for example, secretes few polypeptides to the culture medium. Alternatively, simply treating whole cells expressing the fusion polypeptide with appropriate extraction buffers, as shown in the Examples below, can selectively release the fusion polypeptide without releasing the majority of cytoplasmic polypeptides or nucleic acids. Such selective release greatly simplifies purification of the fusion polypeptide.

A wide variety of polypeptides, including those which are otherwise unstable or largely insoluble, may be expressed as fusions with the IL-1-like polypeptides of the present invention in prokaryotic or eukaryotic cells by employing appropriate expression systems.

In brief, the present invention provides methods and compositions in which a nucleic acid comprising sequences encoding an IL-1-like-polypeptide are fused to a polypeptide of interest, preferably in an expression vector. In the Examples, a T7 RNA polymerase-driven expression system (Studier and Moffat, J. Mol. Biol. 189:113–130, 1986), modified by translational coupling (Squires et al., $J.$ $Biol.$ $Chem.$ 263:16297–16302, 1988), has been utilized to express large quantities of fusion polypeptides in which an IL-1-like polypeptide sequence is attached to the amino terminus of a heterologous polypeptide via a linker polypeptide sequence. Several examples of heterologous polypeptides have been used to show the generic properties of this expression system, including two growth factors, two enzymes, a single-chain antibody, a binding polypeptide and the extracellular domain of a membrane-spanning receptor. The Examples show that the methods and compositions of the present invention enable the high-level soluble expression of certain desirable therapeutic polypeptides, e.g. IGF-I, which are otherwise produced at low levels in bacterial host cells.

The production of fusion polypeptides according to this invention reliably improves the solubility of desired heterologous polypeptides and, by promoting the folding of the desired polypeptides into active conformations and sequestering the fusion polypeptides into a privileged compartment inside or outside the host cell, enhances the stability and accumulation of the heterologous polypeptide products.

Further, the present invention permits the screening of libraries of random polypeptides by assays for their biological function. When fused to an IL-1-like polypeptide, the random polypeptides accumulate in a protected cellular compartment in a soluble, active form. Functional screening of expression libraries containing mammalian DNA has been hampered by the fact that there is no assurance that the desired protein's function is maintained. This problem can easily be obviated by cloning the gene sequences of the library into an expression vector including a sequence for an IL-1-like polypeptide so that the library sequences can be expressed as IL-1 fusions. For example, colonies of $E.$ $coli$ cells transformed with the library are transferred to a solid support such as a nylon membrane. There the cells are gently lysed (e.g., using a mild detergent such as Triton-X 100) to release the expressed fusion polypeptides, and the fusion polypeptides are screened for biological activity which identifies the clone with the gene of interest.

Additionally, the fusion polypeptides of the present invention may be used to develop antibodies, including monoclonal antibodies, by well known methods familiar to those skilled in the art.

Polypeptides

Ordinarily, the IL-1-like polypeptides of the present invention are at least about 20% homologous to the native human IL-1-β polypeptide, preferably at least 40–60%, and more preferably at least about 95% homologous. Such homology is considered to be "substantial homology," although more important than shared amino acid sequence homology is the common possession of the three-dimensional structure characteristic of IL-1.

Polypeptide homology is typically analyzed using sequence analysis software such as the Sequence Analysis Software Package of the Genetics Computer Group, University of Wisconsin Biotechnology Center (1710 University Avenue, Madison, Wis. 53705). Polypeptide analysis software matches similar sequences using measures of homology assigned to various substitutions, deletions, substitutions, and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

A "fragment" of an IL-1-like polypeptide is a portion of a full length IL-1-like polypeptide which substantially retains its functional characteristics. That is, an IL-1-like polypeptide fragment is capable of targeting the polypeptide of interest to which the fragment is fused to the appropriate protected cellular compartment of the host cell in which it is expressed.

"Isolated" The terms "isolated," "substantially pure," and "substantially homogeneous" are used interchangeably to describe a polypeptide which has been separated from its natural components including, for example, a linker sequence, etc., which has been chemically or enzymatically cleaved in order to obtain the polypeptide of interest without such components. A monomeric polypeptide is substantially pure when at least about 60 to 75% of a sample exhibits a single polypeptide sequence. A substantially pure polypeptide typically comprises about 60 to 90% W/W of a polypeptide sample, more usually about 95%, and preferably is over about 99% pure. Polypeptide purity or homogeneity may be indicated by a number of means well known in the art, such as polyacrylamide gel electrophoresis of a polypeptide sample, followed by visualizing a single polypeptide band upon staining the gel. For certain purposes higher resolution can be provided by using HPLC or other means well known in the art.

Polypeptide Purification When expressed in bacterial cells, fusion polypeptides comprising an IL-1-like polypeptide moiety may be released from the cells by modified osmotic shock, freeze/thaw procedures, or by resuspension in certain extraction buffers, as exemplified below. Further polypeptide purification can be accomplished by various methods well known in the art, e.g., affinity chromatography.

It may be advantageous to cleave the fusion polypeptide in order to isolate a polypeptide of interest away from an IL-1-like fusion partner and/or linker sequence or other sequences comprising the fusion polypeptide of which it is a part. A linker comprising a sequence encoding a polyhistidine stretch, for example, can be purified by binding to a resin such as Ni-NTA resin (QIAGEN, Chatsworth, Calif.) and ProBond resin (Invitrogen, San Diego, Calif.). Other useful methods of polypeptide purification are described, e.g., in *Guide to Polypeptide Purification,* ed. M. Deutscher, 182 Meth. Enzymol. (Academic Press, Inc.: San Diego, 1990) and R. Scopes, *Polypeptide Purification: Principles and Practice,* Springer-Verlag: New York, 1982.

Preferably, cleavage of the fusion polypeptide occurs in vivo via the co-expression of a compatible proteolytic enzyme in the cytoplasm of the host cell. In bacterial hosts such as *E. coli,* ubiquitin hydrolase is preferred. When expressed along with a polypeptide having a ubiquitin hydrolase cleavage site, e.g., as part of a linker in the fusion genes of the present invention, ubiquitin hydrolase cleaves specifically and efficiently, as demonstrated in Example 6.

The intact fusion polypeptide may also be useful. For example, a fusion of human interleukin-1-β, or its analogues, to a second polypeptide may have therapeutic uses.

Polypeptide modifications; fragments; fusion polypeptides The present invention also provides for polypeptides or fragments thereof which are substantially homologous to the primary structural sequence of the human IL-1-β polypeptide. The present invention also embraces polypeptides with in vivo or in vitro chemical and biochemical modifications or which incorporate unusual amino acids. Such modifications are well known and include, for example, acetylation, carboxylation, phosphorylation, glycosylation, ubiquitination, labelling, e.g., with radionuclides, various enzymatic modifications. See, e.g., *Molecular Cloning: A Laboratory Manual,* 2nd ed., Vol. 1–3, ed. Sambrook, et al., Cold Spring Harbor Laboratory Press (1989) or *Current Protocols in Molecular Biology,* ed. F. Ausubel et al., Greene Publishing and Wiley-Interscience: New York (1987 and periodic updates).

The present invention provides fusion polypeptides comprising an IL-1-like polypeptide and any polypeptide of interest. Examples of polypeptides fused to an IL-1-like polypeptide include any peptide or polypeptide useful for human or veterinary therapy, diagnostic or research applications. Such polypeptides of interest include but are not limited to hormones, cytokines, growth or inhibitory factors, and enzymes.

The IL-1-like polypeptides, polypeptides of interest and fusion polypeptides are typically made by recombinant methods but may be chemically synthesized. Techniques for synthesis of polypeptides are described, for example, in Merrifield, *J. Amer. Chem. Soc.* 85:2149–2156, 1963.

Nucleic Acids

The present invention provides nucleic acids which encode a fusion polypeptide comprising an IL-1-like polypeptide and another polypeptide of interest. Such nucleic acids include RNA, cDNA, genomic DNA, synthetic forms, and mixed polymers, both sense and antisense strands. Such nucleic acids can be chemically or biochemically modified and can contain non-natural or derivatized nucleotide bases. The sequence encoding the fusion polypeptide can be interrupted by introns.

The nucleic acid sequences of this invention are of a length sufficient to encode such a fusion polypeptide and, if necessary, any vector sequences. The sequences are usually several hundred nucleotides or nucleotide base pairs in length and may be several kilobases long.

Techniques for nucleic acid manipulation, including the construction of nucleic acids capable of encoding and expressing the fusion polypeptides of the present invention, are well known and are described generally, for example, in Sambrook et al., op. cit., or Ausubel et al., op. cit. Reagents useful in applying such techniques, such as restriction enzymes and the like, are widely known in the art and commercially available.

The recombinant nucleic acid sequences used to produce fusion polypeptides of the present invention may be derived from natural or synthetic sequences. The nucleotide sequences and amino acid sequences and/or fragments thereof may be obtained from GENBANK and/or the Swiss Protein Database, with the database accession numbers as follows:

| Gene | GENBANK | Swiss-Prot |
|---|---|---|
| IGF | HUMIGFI | |
| | SYNHUMGFIS | |
| ubiquitin | YSCUBI1G | UBIQ_YEAST |
| | YSCUBI2G | |
| | YSCUBI3G | |
| | YSCUBI4G | |
| ubiquitin hydrolase | YSCUBP1 | |
| Il-1-β | HUMIL1AA | IL1B_HUMAN |
| IL-1-RA | HSI1RA | |
| IL-1-α | HUMIL1AA | |
| | AGHSIL1A | |
| FGF-β | HUMFGFB | |
| TGF-β | | TGF2_HUMAN |
| TGF-β-receptor II | HUMTGFBIIR | |
| IGFBP-3 | | IBP3_HUMAN |
| TcpG | VCDSBAG | |
| EGF-binding kallikrein | MUSEGFBPB | |

In the case of IGF and IGFBP-3, codon-optimized genes were employed. In all cases only the portions of each sequence coding for the mature gene product were used.

The nucleotide sequences of various IL-1-like polypeptides have also been reported, e.g., in: Maliszewski et al., *Mol. Immunol.* 25:429–437, 1988; Auron et al., *Proc. Natl. Acad. Sci. U.S.A.* 81:7907–7911, 1984; March et al., *Nature (Lond.)* 315:641–647, 1985; Lomedico et al., *Nature (Lond.)* 312:45.8–462, 1984; Gray et al., *J. Immunol.* 137:3644–3648, 1986; Nishida et al. in *Monokines and Other Nonlymphocytic Cytokines,* eds. Powanda et al. (Liss, N.Y.), pp. 73–78, 1988; Furutani et al., *Nucl. Acids Res.* 13:5869–5882, 1985; Mori et al., *Biochem. Biophys. Res. Commun.* 150:1237–1243, 1988 (IL-1-α and IL-1-β from human, mouse, rat, bovine and rabbit); Eisenberg et at., *Proc. Natl. Acad. Sci. U.S.A.* 88:5232–5236, 1991 (human, mouse, and rat IL-1ra); and Bardwell et al., *Cell* 67:581–589, 1991 (*E. coli* DsbA). These references are herein incorporated by reference.

Other sequences employed in the construction of the fusion polypeptides of the present invention include the soluble extracellular domain of the Type II TGF-β receptor (Lin et al., *Cell* 68:775–785, 1992) and EGF-binding kallikrein (Blaber et al., *Biochemistry* 26:6742–6749, 1987). Any expression vector compatible with a chosen host cell may be employed in the practice of the present invention.

Construction of the fusion polypeptides of the present invention is readily accomplished using well known methods in recombinant DNA technology, e.g., PCR, automated DNA synthesis, etc.

"Encode" A nucleic acid is said to "encode" a polypeptide if, in its native state or when manipulated by methods well known to those skilled in the art, it can be transcribed and/or translated to produce the polypeptide. The anti-sense strand of such a nucleic acid is also said to encode the polypeptide.

"Operably linked" A nucleic acid sequence is operably linked when it is in a functional relationship with another nucleic acid sequence. For instance, a promoter is operably linked to a coding sequence if the promoter affects its transcription or expression. Generally, operably linked means that the DNA sequences being linked are contiguous and, where necessary to join two polypeptide coding regions, contiguous and in reading frame.

"Recombinant" The term "recombinant" nucleic acid (and by analogy, a "recombinant" polypeptide produced by the expression of a recombinant nucleic acid) is one which is not naturally occurring or is made by the artificial combination of two otherwise separated segments of sequence by chemical synthesis means or the artificial manipulation of isolated segments of nucleic acids, e.g., by genetic engineering techniques.

Preparation of recombinant or chemically synthesized nucleic acids; vectors, transformation, host cells Large amounts of the nucleic acids of the present invention may be produced by replication in a suitable host cell, whether bacterial, yeast, insect, amphibian, avian, mammalian or other eukaryotic cells and expression systems. The natural or synthetic DNA fragments coding for a desired fragment will be incorporated into recombinant nucleic acid constructs, typically DNA constructs. These DNA constructs are introduced into prokaryotic or eukaryotic cells where they replicate. Usually the DNA constructs are suitable for autonomous replication in a unicellular host, such as yeast or bacteria. The constructs also can be introduced to and integrated within the genome of a cultured insect, mammalian, plant or other eukaryotic cell lines. Suitable methods for these purposes are well known in the art and have been described, e.g., in Sambrook et al. (1989) or Ausubel et al. (1987 and periodic updates).

The nucleic acids of the present invention are optionally produced by chemical synthesis, e.g., by the phosphoramidite method described by Beaucage and Carruthers (*Tetra. Letts.* 22:1859–1862, 1981) or the triester method according to Matteucci et al. (*J. Am. Chem. Soc.* 103:3185, 1981) and may be performed on commercial automated oligonucleotide synthesizers.

DNA constructs prepared for introduction into a prokaryotic or eukaryotic host typically comprise a replication system recognized by the host, including the intended DNA fragment encoding the desired polypeptide, and preferably also include transcription and translational initiation regulatory sequences operably linked to the polypeptide encoding segment. Expression vectors include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors are prepared by means of standard recombinant techniques well known in the art and discussed, for example, in Sambrook et al. (1989) or Ausubel et al. (1987).

Appropriate promoter and other necessary vector sequences are selected to function in the host. Examples of functional combinations of cell lines and expression vectors are described in Sambrook et al., 1989 or Ausubel et al., 1987); see also, e.g., Metzger et al., *Nature* 334:31–36, 1988. Many useful vectors are known in the art and are commercially available. For use in prokaryotic hosts, promoters include but are not limited to the trp, lac and phage promoters, tRNA promoters and glycolytic enzyme promoters. Useful yeast promoters include but are not limited to the promoter regions for metallothionein, 3-phosphoglycerate kinase or other glycolytic enzymes such as enolase or glyceraldehyde-3-phosphate dehydrogenase, and enzymes responsible for maltose and galactose utilization. Other suitable vectors and promoters for use in yeast expression are further described in Hitzeman et al. EP 73,657A. Appropriate nonnative mammalian promoters include but are not limited to the early and late promoters from SV40 (Fiers et al. *Nature* 273:113, 1978) or promoters derived from murine molony leukemia virus, mouse mammary tumor virus, avian sarcoma viruses, adenovirus II, bovine papilloma virus and polyoma virus. In addition, the construct can be joined to an amplifiable gene (e.g., DHFR) so that multiple copies of the gene are made.

Such expression vectors can replicate autonomously. In a less preferred mode, the expression vector can replicate by being inserted into the genome of the host cell, by methods well known in the art.

Expression and cloning vectors generally include a selectable marker, which encodes a polypeptide necessary for the survival or growth of its host cells. This gene's presence ensures the growth of only host cells expressing the marker. Typical selection genes encode polypeptides that (a) confer resistance to antibiotics or other toxic substances, e.g. ampicillin, neomycin, methotrexate, etc.; (b) complement auxotrophic deficiencies; or (c) supply critical nutrients not available from complex media. The choice of the proper selectable marker depends on the host cell. Appropriate markers for different hosts are well known in the art.

Vectors with the nucleic acids of interest can be transcribed in vitro, and the resulting RNA are introduced into host cells by well known methods (e.g., by injection). See, T. Kubo et al., *FEBS Lett.* 241:119, 1988. Alternately, the vectors can be introduced directly into host cells by methods well known in the art, which vary depending on the type of cellular host. These methods include but are not limited to electroporation; transfection employing calcium chloride, rubidium chloride calcium phosphate, DEAE-dextran, or other substances; microprojectile bombardment; lipofection; and infection (where the vector is an infectious agent, such as a retroviral genome). See generally, Sambrook et al. (1989) and Ausubel et al. (1987). The so-transformed cells are also meant to include the progeny of such cells.

Large quantities of the nucleic acids and polypeptides of the present invention are prepared by expressing the nucleic acids or portions thereof in vectors or other expression vehicles in compatible prokaryotic or eukaryotic host cells. The most commonly used prokaryotic hosts are strains of *E. coli,* although other prokaryotes, such as *Bacillus subtilis* or *Pseudomonas,* may also be used. Mammalian or other eukaryotic host cells, such as those of yeast, filamentous fungi, plant, insect, amphibian or avian species, may also be useful for production of the polypeptides of the present invention.

The invention has been disclosed by direct description. The following are examples showing the efficacy of the method in producing soluble, active polypeptides. The examples are only examples and should not be taken in any way as limiting to the scope of the invention.

EXAMPLES

Example 1: Expression and purification of fusion proteins

The following materials and methods used throughout the Examples unless otherwise indicated. Further details can be found in the references cited herein.

Bacterial strains and growth conditions. E. coli JM109 F- traD36 lacIq del(lacZ)M15 proAB/recA1 endal gyrA96 thi hsdR17 supE44 relA1 del(lac-proAB).

E. coli W3110 DE3 F- thi (lambda DE3 lysogen; Studier and Moffat, J. Mol. Biol. 189:113–130, 1986).

These strains were grown in L-Broth at 37° C. with aeration unless otherwise indicated. For plasmid-containing strains, antibiotics were added to the growth medium as appropriate.

Plasmids. The expression vectors used in this work are essentially identical to pJU1003 (Squires et al., J. Biol. Chem. 263:16297–16302, 1988), except that sequences were inserted downstream of the translational coupler and initiation codon which code for various configurations of the following genes: mature human IGF-1 (70 aa), IGFBP-3 (264 aa), TGF-β2 (112 aa), TGF-β-receptor (extracellular domain, 136 aa), or mouse EGF-binding kallikrein (237 aa). In each case a termination codon follows these sequences. These plasmids also differ from pJU1003 in that (a) they do not contain the synthetic 16 bp adaptor sequence at the 5' end of the tet gene in pJU1003; and (b) they contain a DNA insertion at the unique PvuII site in the pBR322-derived backbone consisting of a 385 bp fragment containing the par locus of pSC101 (Meacock and Cohen, Cell 20:529–542, 1980). The plasmids also contain a gene encoding a leaderless E. coli periplasmic rotamase downstream of the foreign gene and within the same transcriptional unit. The signal sequence of the rotamase gene was deleted as described by Liu and Walsh, Proc. Natl. Acad. Sci. U.S.A. 87:4028–4032, 1990, and replaced with an initiator methionine codon. The presence of a truncated rotamase gene neutralizes the growth inhibitory effect of ubiquitin fusions in E. coli host cells, as disclosed in co-pending application filed on even date and entitled "Methods and DNA Expression Systems for Over-Expression of Proteins in Host Cells" with attorney's Docket No. designated 22095-20266.00.

Each gene was prepared for expression in four separate configurations to yield the plasmids listed in Table 1: (1) with the 76 codons of yeast ubiquitin ("Ubi") inserted in-frame with and upstream of the gene sequence; (2) with the 153 codons for mature human IL-1-β ("IL1β") fused in-frame between the initiation codon and the gene, and with a linker encoding Asp-Arg-Gly-Gly (SEQ ID NO:6) inserted between the IL-1-β sequence and the gene sequence; (3) with the 76 codons of yeast ubiquitin inserted between the linker and the gene sequence of configuration (2); and (4) with the 189 codons of mature E. coli DsbA followed by a linker encoding His-His-His-His-His-His-Ser (SEQ ID NO:7), replacing the IL-1-β plus linker sequences of configuration (3). In addition, vectors 12886 and 12887 in which the gene is deleted and replaced with a linker (5' . . . G G A T C C C G T G G A G G A T T A A A C C A T G G A T- G C A T A A G C T T C G A A T T C T G C C A G G C A T G- CAAGCTCAGATCC . . . 3' (SEQ ID NO:8)) are used as controls.

Six plasmids—pYZ22070, pYZ22096, pYZ9205, pYZ9206, pDM15426, and pDM15424—contain the T7 transcriptional unit of the above plasmids in a pACYC184 backbone (Chang and Cohen, J. Bacteriol. 134:1141–1156, 1978). Specifically, in these six plasmids, the ClaI-ScaI fragment carrying the T7 promoter, the translational coupler, the gene construct, the rotamase gene and the T7 terminator replaced the 1.0 kb ClaI-NruI fragment of pACYC184. The pYZ9205 plasmid contains the complete coding sequence for DsbA in the above vector backbone. The pYZ9206 plasmid is identical to pYZ9205 except that the signal sequence of DsbA has been replaced by a methionine codon. The pDM15426 plasmid is identical to pYZ22070 (above) except that it includes the signal sequence of DsbA. The pDM15424 plasmid contains the coding sequence for IL-1-receptor antagonist without its natural signal sequence.

TABLE 1

| | Gene | | | | |
|---|---|---|---|---|---|
| Config. | IGF-I | IGFBP-3 | TGF-β2 | TGFR | EGFBP |
| #1 | pDJ16927 | pDJ12875 | pDJ16920 | pDJ16921 | pDJ9667 |
| #2 | pDM16963 | pDM16964 | pDM16973 | pDM16962 | pDM16972 |
| #3 | pDM16965 | pDM16967 | pDM16977 | — | pDM16976 |
| #4 | pYZ22070 | pDM15427 | pYZ22096 | pDM15428 | pDM15429 |

Yeast ubiquitin and rotamase sequences were obtained using PCR-mediated amplification from the appropriate genomic DNAs. cDNA clones for IGFBP-3 were isolated as described in Spratt et al., Growth Factors 3:63–72, 1990, and further modified by substituting the amino-terminal one-third of the gene with a synthetic DNA sequence encoding the same amino acids as the natural gene (namely, the initial 288 nucleotides of the mature sequence, up to the unique BssHII site), but using codons optimized for expression in E. coli (see, for example, Fiers, Nature 260:500, 1976). The IGF-I sequence was constructed de novo from synthetic DNA and likewise used codons optimized for E.coli.

The TGF-β2 sequence was obtained by PCR-mediated modification of a CDNA clone obtained from Dr. Michael Sporn, National Institutes of Health. The TGF-β-receptor sequence was similarly derived from pH2-3FF, a CDNA clone from Dr. Herb Lin, Massachusetts Institute of Technology, and the mouse EGF-binding kallikrein sequence from pMS2-12A, a cDNA clone from Dr. Ralph Bradshaw, University of California at Riverside. All PCR-derived DNAs were sequenced prior to use.

Each plasmid was introduced into W3110DE3 by calcium chloride-mediated transformation and selection for antibiotic resistance.

Enzymes and reagents. Enzymes and reagents were purchased from New England Biolabs, Beverly, Mass.; Boehringer Mannheim, Indianapolis, Ind.; Sigma Chemical Co., St. Louis, Mo.; Pharmacia, Piscataway, N.J.; BRL, Gaithersburg, Md.; US Biochemical, Cleveland, Ohio; and Clontech, Palo Alto, Calif.

General techniques. Restriction digests, agarose gel electrophoresis, ligations, transformations, DNA preparation, DNA sequencing, cell culture, SDS-PAGE, Western Blots, ELISA, and other common molecular biological techniques are described in Maniatis et al., *Molecular Cloning: A Laboratory Manual,* 2d ed., Vols. 1–3, ed. by Sambrook et al., Cold Spring Harbor Laboratory Press, 1989 and *Current Protocols in Molecular Biology,* ed. F. Ausubel et al., Greene Publishing and Wiley-Interscience: New York, 1987 and periodic updates.

Cell growth and harvest. *E. coli* strain W3110 DE3 containing one of the above plasmids was introduced into 5 ml Luria Broth (LB) containing tetracycline (15 $\mu$g/ml) or chloramphenicol (20 $\mu$g/ml) and grown to saturation overnight with aeration at 37° C. Two ml of fresh overnight culture was diluted into 100 ml of LB supplemented with 0.2% glucose. The culture was grown with aeration for several hours at the same temperature. The optical density of the culture was followed through early logarithmic growth until the optical density (600 nm) reached 0.4. Then a one ml aliquot was removed and the cells were harvested ("0 minutes" time point).

Isopropyl-thiogalactopyranoside (IPTG) was added to a final concentration of 0.4 mM and incubation of the culture continued for two hours. A second aliquot of cells was removed ("120 minutes" time point).

Aliquots from these time points were used to prepare "Whole Cell Lysates" (WCL) as described below. The remainder of the culture was harvested by centrifugation, then treated by (1) the "TEX buffer extraction" protocol or (2) a variant of the TEX protocol without the TEX step, the "simple sonication protocol."

TEX buffer extraction protocol. Cells were resuspended in 1/10th of the original culture volume of TEX buffer (50 mM Tris-Cl, pH 8.0, 2 mM EDTA, 0.1% Triton X-100) and placed on ice for 20–60 minutes. After centrifugation in a Beckman TJ-6 centrifuge at 3,000 rpm for 15 minutes at 4° C., the supernatant ("TEX extract" or "T" in the Figures) was removed, and the cell pellet was resuspended in the same volume of TE (10 mM Tris-Cl, pH 8.0, 1 mM EDTA). Cells were disrupted by sonication using a Branson sonifier (2×30 sec bursts). In some experiments, lysis was enhanced by adding 0.2 mg/ml chicken lysozyme to the disruption buffer, although this step did not appear to be necessary. The disrupted cells were centrifuged in a Beckman TJ-6 centrifuge at 3,000 rpm for 15 min at 4° C. The supernatant ("cytoplasmic fraction", or "C" in the Figures) was removed. The pellet was washed once in TE and further resuspended in an equal volume of TE buffer ("insoluble fraction", or "I" in the Figures) for analysis.

Simple sonication protocol. Cells were resuspended in 1/10th of the original culture volume of TE (10 mM Tris-Cl, pH 8.0, 1 mM EDTA), and sonicated. All subsequent steps were the same as for the TEX buffer extraction protocol after sonication. However, the supernatant obtained after sonication in this protocol is referred to as the "soluble" fraction (labelled "S" in the Figures) (and represents the sum of the "TEX" and "cytoplasmic" fractions).

Whole cell extracts were prepared for electrophoresis by resuspending each whole cell aliquot removed from the culture during growth in 100 $\mu$l SDS-PAGE sample buffer and boiling for 5 minutes. "Soluble" and "insoluble" fraction samples were prepared by adding one volume of 2× sample buffer (1% SDS, 10% glycerol, 0.1% bromphenol blue) and incubating at 65° C. for 15 minutes.

Example 2: Homology between IL-1-like proteins

FIG. 1 shows an alignment of the sequences of five members of the IL-1-like protein family: (1) *E. coli* DsbA, (2) human IL-1-$\beta$, (3) human IL-1-$\alpha$, and (4) human basic and (5) human acidic fibroblast growth factors (FGFs). To maximize the alignment, the appropriate regions of the longer members were excluded from the comparison, notably the oxidoreductase active site loop of DsbA (residues 21–35), and another large loop elsewhere in DsbA (residues 126–157).

Figure 2:
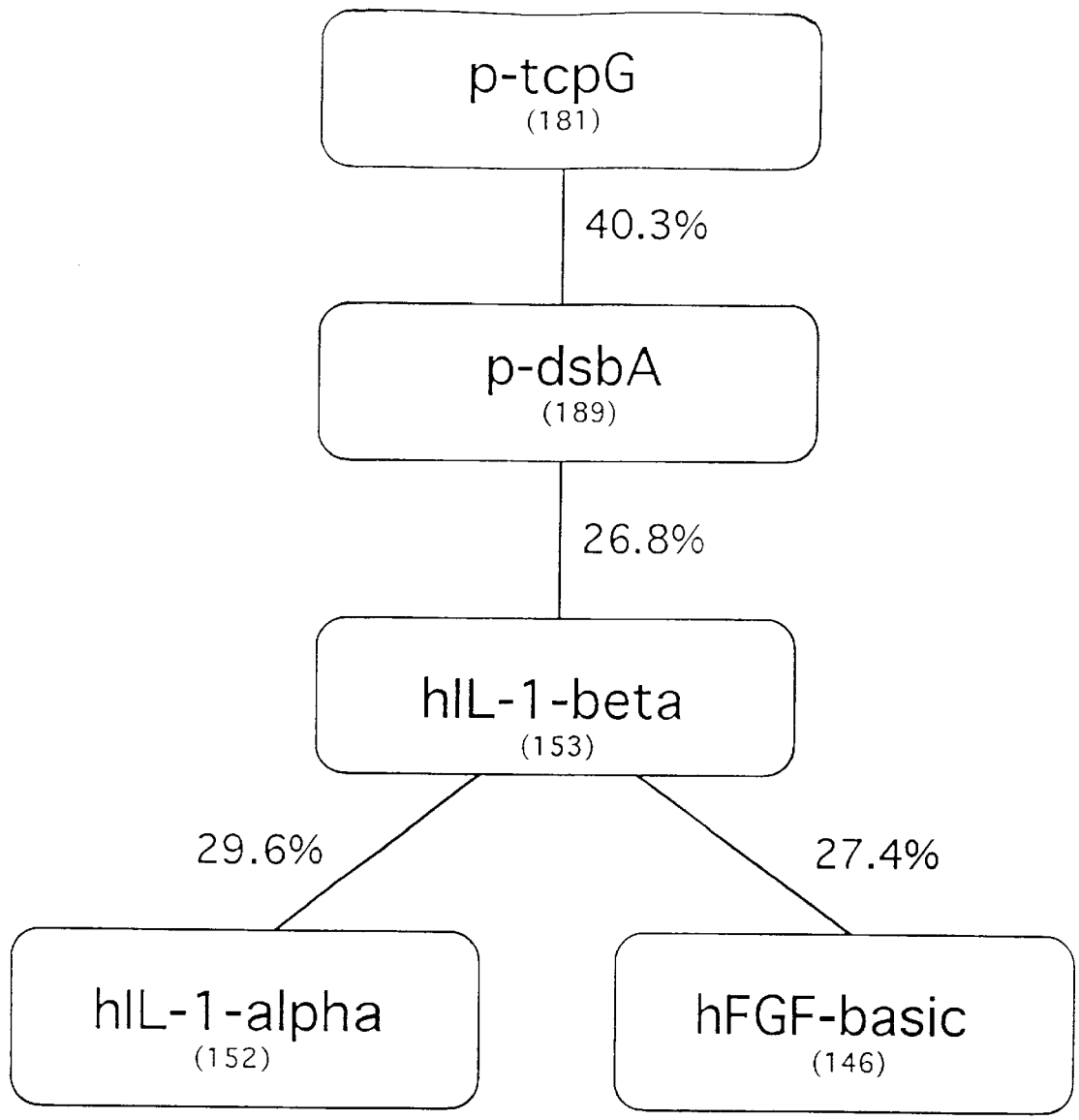
FIG. 2 summarizes the homologies between the mature polypeptides of *E. coli* DsbA, human IL-1-β, human IL-1-α, human basic fibroblast growth factor (FGF), and the toxin coregulated pilus (TcpG) polypeptide of *Vibrio cholerae.* The size of each of the mature polypeptides is given in parentheses.
Figure 3A:
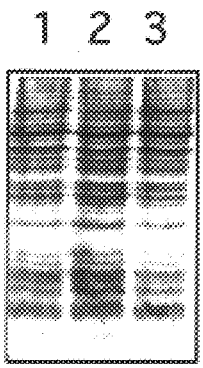
FIG. 3 shows Coomassie stained SDS-PAGE gels of fractions from *E. coli* cells grown at 37° C. in which IL-1-β is expressed. A: whole cell lysates ("WCL"), at time 0 (0'); B: WCL, 120 min (120'); C: TEX extract; D: "cytoplasmic" fraction; E: "insoluble" fraction. For each gel, lane 1 is wild-type IL-1β, lane 2 is IL-1β triple mutant R4A, L6A, R11G, and lane 3 is IL-1β triple mutant R4D L6A R11G. The expected size of wild-type or mutant IL-1β in each case is approximately 17 kD (•).
Figure 3B:
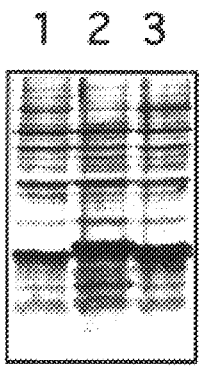
Figure 3C:
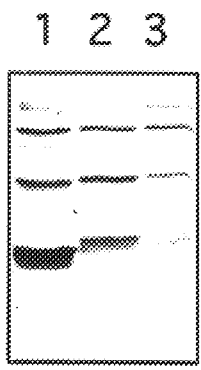
Figure 3D:
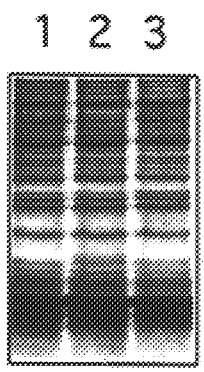
Figure 3E:
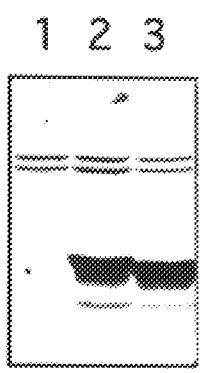
Figure 4A:
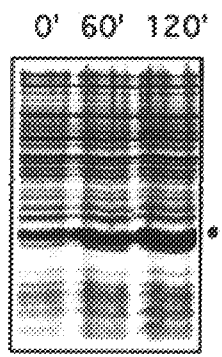
FIG. 4 shows SDS-PAGE of fractions from *E. coli* cells expressing *E. coli* DsbA. (a) WCL at 0', 60', and 120' from cells expressing mature DsbA; (b) WCL at 0', 60', and 120' from cells expressing "mutant" DsbA; (c) TEX extract ("T") and "cytoplasmic" ("C") fractions from cells expressing mature DsbA; (d) "T" and "C" fractions from cells expressing "mutant" DsbA. The expected size of the expressed polypeptide is approximately 22 kD (•).
Figure 4B:
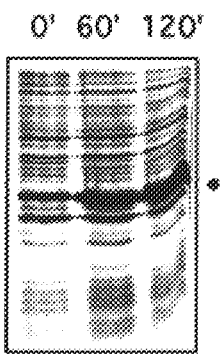
Figure 4C:
Figure 4D:
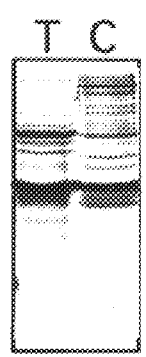

When optimally aligned in this fashion, the various members of this group and the toxin coregulated pilus (TcpG) polypeptide, a bacterial homolog of *E. coli* DsbA from Vibrio cholerae (Peek and Taylor, op. cit.), exhibit the homologies to IL-1-$\beta$ shown in FIG. 2. In addition to the noted homologies, several conservative substitutions may be observed at various positions in the sequences shown in FIG. 1, for example, Ile→Val, Phe→Tyr, and Asp→Glu at several positions.

Example 3: Accumulation and Preferential release of IL-1-like polpeptides and fusions thereof from bacterial cells Three representative members of the IL-1-like protein family were chosen to exemplify the widespread applicability of polypeptide fusions to IL-1-like polypeptides in order to achieve the accumulation and preferential release of the fusion proteins from bacterial cells: (1) human IL-1-$\beta$, (2) human IL-1-receptor antagonist (IL-1ra), and (3) *E. coli* DsbA. Mature sequences of IL-1ra and *E. coli* DsbA were expressed, i.e., their naturally encoded amino-terminal signal sequences were replaced with a single initiator methionine codon (pDMi5424 and pYZ920[6]; p154[33] is identical to pY9206, except that codons V22 to Q35 of DsbA were replaced with codons V22 to P77 of gene III from bacteriophage m13; the expected size of the mutant gene product is approximately 27 kD). For IL-1-$\beta$, the 153 codons specifying the mature protein were placed downstream of an initiator methionine codon (pDJ12151).

FIG. 3 shows the results of the fractionation by SDS-PAGE of *E. coli* cells in which IL-1-$\beta$ is expressed and grown at 37° C. FIG. 3A shows whole cell lysates ("WCL") from cells at the 0 minute timepoint; FIG. 3B, WCL, 120 minutes; FIG. 3C, TEX extract; FIG. 3D, "cytoplasmic" fraction; and FIG. 3E, "insoluble" fraction. For each gel, lane 1 is wild-type IL-1$\beta$, lane 2 is IL-1$\beta$ triple mutant R4A, L6A, R11G), and lane 3 is IL-1$\beta$ triple mutant R4D L6A R11G. These two triple mutants are modified at residues which abolish the biological activity of IL-1-$\beta$ without affecting IL-1-$\beta$ binding to at least one of its natural receptors (Gehrke et al., *J. Biol. Chem.* 265:5922–5925, 1990; Labriola-Tomkins et al, *Proc. Natl. Acad. Sci. U.S.A.* 88:11182–11186, 1991). The expected size of wild-type or mutant IL-1$\beta$ in each case is approximately 17 kD (indicated with a • to the right of each gel).

These gels indicate that the majority of the expressed wild-type IL-1-$\beta$ (lane 1 of FIGS. 3A–E) was found in the TEX fraction, demonstrating that IL-1-$\beta$ was sequestered to a non-cytoplasmic location in vivo. This was not the case with the two triple mutants (R4A L6A R11G, lane 2; and R4D L6A R11G, lane 3). The majority of the expressed IL-1-$\beta$ from these mutants was found in the "insoluble"

fraction. These data indicate that even subtle modifications affect the ability of IL-1-β to accumulate in a non-cytoplasmic, soluble form.

The data in Table 2 (below) confirm these results, showing that an IL-1-β-IGF fusion, like IL-1-β itself, is found almost exclusively in the TEX fraction, along with beta-lactamase, a periplasmic protein. Only a small percentage of the IL-1-β-IGF fusion protein co-localizes with beta-galactosidase, a cytoplasmic marker.

FIG. 4 shows the accumulation and SDS-PAGE fractionation of E. coli DsbA. FIG. 4a shows whole cell lysates ("WCL") at 0, 60, and 120 minute timepoints from cells expressing mature DsbA (i.e., lacking a signal sequence); FIG. 4b, WCL at 0, 60, and 120 minute timepoints from cells expressing a "mutant" mature DsbA with a replacement of the active site loop by approximately 55 amino acids from gene III of bacteriophage m13 (codons V22 to Q35 of DsbA were replaced with codons V22 to P77 of m13 gene III); FIG. 4c, TEX extract ("T") and "cytoplasmic" ("C") fractions from cells expressing wild-type mature DsbA; and FIG. 4d, "T" and "C" fractions from cells expressing "mutant" DsbA. The expected size of the expressed polypeptide is approximately 22 kD.

Again, virtually all the expressed DsbA protein was found in the TEX fraction. The ability to transfer to an extractable compartment was not lost when the "active" site loop of DsbA was replaced by sequences from an unrelated gene.

Figures 5A, 5B, 5C, 5D, 5E, 5F, 5G, 5H:
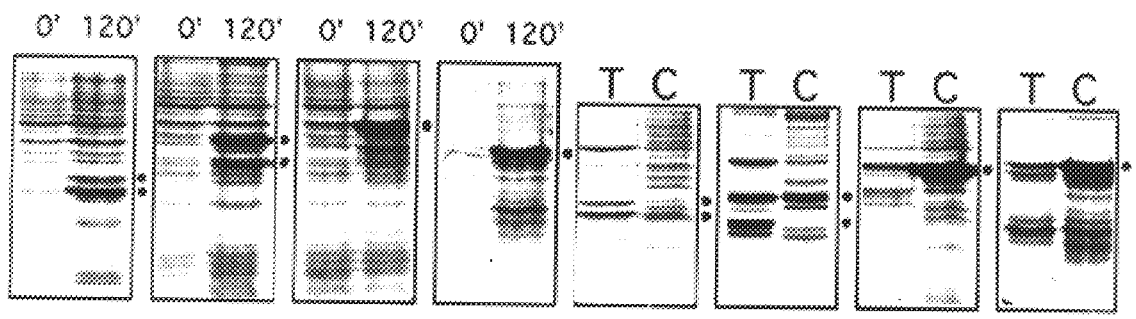
FIG. 5 shows SDS-PAGE gels of fractions from *E. coli* cells in which various fusions of IL-1-like proteins with human IGF-I or the soluble extracellular domain of the Type II TGF-β receptor were expressed. Left: WCL at 0' and 120' for (1) IL1β-IGF (pDM16963), expected size approximately 24–25 kD; (2) IL1β-Ubi-IGF (pDM16965), expected size approximately 32 kD (•); (3) DsbA-Ubi-IGF (pYZ22070), expected size approximately 37 kD (•); and (4) DsbA-Ubi-TGFR (pDM15428), expected size approximately 46 kD (•). Right: TEX and "cytoplasmic" ("CYT") fractions for the four fusion polypeptides. Where there are two dots, the lower dot represents a lower molecular weight breakdown product of the larger polypeptide.

FIG. 5 shows the fractionation of cells in which various fusions of IL-1-like proteins with human IGF-I or TGF-β receptor were expressed: (1) IL1-IGF (pDM16963), with an expected size of approximately 24–25 kD); (2) IL1β-Ubi-IGF (pDM16965), with an expected size of approximately 32 kD; (3) DsbA-Ubi-IGF (pYZ22070), with an expected size of approximately 37 kD; and (4) DsbA-Ubi-TGFR (pDM15428), with an expected size of approximately 46 kD.

The four SDS-PAGE gels in FIG. 5, left, show WCL at 0 and 120 minute timepoints of E. coli cells expressing these four fusion polypeptides. The four SDS-PAGE gels in FIG. 5, right, show TEX and "cytoplasmic" fractions for these four fusion polypeptides. Dots are used to denote the band of the fusion polypeptide and when there is a second dot present, the presence of a breakdown product of the fusion polypeptide.

In all four cases substantial proportions of the fusion proteins were found in the TEX fraction. Thus, these fusions of IL-1-like proteins from cells also substantially transferred to the extractable compartment.

Figure 6A:
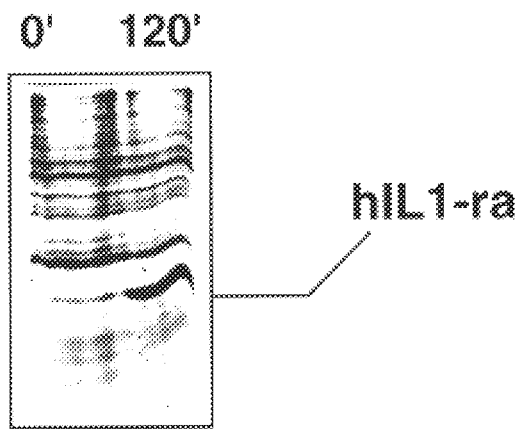
FIG. 6 shows SDS-PAGE of fractions from *E. coli* cells expressing human IL-1-receptor antagonist with its natural signal sequence deleted (pDM15424). Left: WCL at 0' and 120'; right, TEX ("T") and "cytoplasmic" ("C") fractions ("FXN"). The expected product has a size of approximately 18 kD.
Figure 6B:
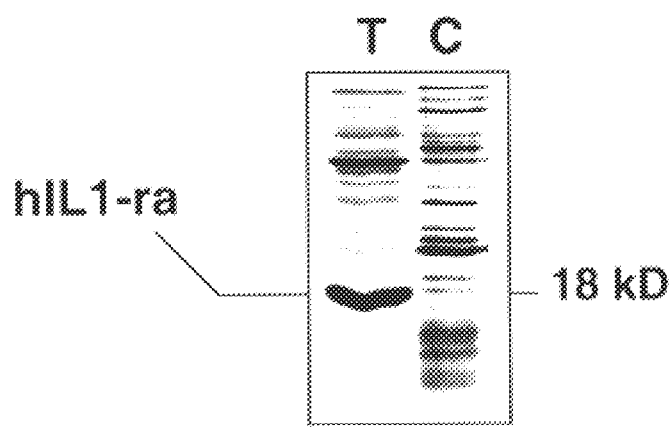

FIG. 6 shows whole cell lysates ("WCL") at 0 and 120 minute timepoints and TEX ("T") and "cytoplasmic" ("C") fractions ("FXN") of human IL-1-receptor antagonist expressed in E. coli with its natural signal sequence deleted (pDM15424). Again, most of the protein was found in the TEX fraction. This result indicates that IL-1-ra lacking a signal sequence is properly secreted.

Table 2 (below) shows that the TEX fractions of E. coli cells expressing IL-1-β or an IL-1-β-IGF fusion contained a periplasmic enzyme marker, β-lactamase, but not a cytoplasmic marker, β-galactosidase. In the same samples, Il-1 immunoreactivity (signifying the presence of the fusion protein) was found almost exclusively in the TEX fraction.

TABLE 2

Percent of Total Cell Activity

| Assay | pDJ12151 (IL-1-β) | | pDM16963 (IL-1-β-IGF) | |
|---|---|---|---|---|
| | TEX | CYT | TEX | CYT |
| Beta-lactamase | 96.4 | 3.6 | 96.1 | 3.9 |
| Beta-galactosidase | 2.3 | 97.7 | 6.5 | 93.5 |
| Interleukin-1-β | 94.1 | 5.9 | 93.2 | 6.8 |

To confirm a similar localization with mature DsbA, oxidoreductase assays were performed on crude extracts as described by Holmgren (J. Biol. Chem. 254:9627–9632, 1979), except for the following modifications: Assays were performed at room temperature; DTT was at 0.1 mM; and insulin substrate was at 1 mg/ml. The results are provided in Table 3. Like IL-1-ra, DsbA lacking a signal sequence is secreted, resulting in its localization in the TEX fraction.

TABLE 3

Oxidoreductase Activity of DsbA

| Signal Sequence | Fraction | Activity (U/min-mg) | Percent Total Cell Activity |
|---|---|---|---|
| + | T | 0.089 | 87.3 |
| + | C | 0.013 | 12.7 |
| − | T | 0.100 | 89.3 |
| − | C | 0.012 | 10.7 |

T = TEX fraction; C = cytoplasmic fraction

Example 4: Accumulation of soluble fusion polypeptides in bacteria

IL-1-like fusion partners conferred a pronounced and salutary effect on the solubility of a variety of structurally unrelated heterologous proteins expressed in bacteria.

FIGS. 7 through 10 summarize the results obtained when the "soluble" (S) and "insoluble" (I) fractions of induced cells carrying constructs for each of four different human genes were compared.

In FIG. 7, TGF-β2 fusion constructs were analyzed. FIG. 7, left, shows Coomassie-stained SDS-polyacrylamide gels of whole cell lysates ("WCL") from 0 and 120 minute timepoints and soluble ("S") and insoluble ("I") fractions from E. coli cells which are transformed with pDJ16920, which encodes a ubiquitin-TGF-β2 fusion polypeptide with an expected size of approximately 20 kD. Virtually all of this fusion polypeptide was found in the "insoluble" fraction. However, with plasmid pYZ22096 encoding a DsbA-ubiquitin-TGF-β2 fusion of approximately 42 kD, FIG. 7, right, shows the protein was almost entirely soluble. These results are also significant in that they show that soluble TGF-β2 may be obtained at 37° C. Previous attempts to obtain soluble TGF-β2 relied on low temperature growth (e.g., at 30° C.), which is less desirable since lower temperature growth is suboptimal for growth of E. coli host cells and requires expensive reactor cooling.

In FIG. 8 the results obtained with several IGF-I fusions are displayed. FIG. 8, left, shows Coomassie-stained SDS-polyacrylamide gels of whole cell lysates ("WCL") from 0 and 120 minute timepoints and soluble ("S") and insoluble ("I") fractions from E. coli cells transformed with pDJ16927 and pDM16965. pDJ16927 expresses a ubiquitin-IGF fusion with an expected size of approximately 15 kD. pDM16965 expresses IL1-ubiquitin-IGF with an expected size of approximately 32 kD.

FIG. 8, right, shows similar gels of extracts of E. coli cells transformed with pYZ22070, which expresses mature DsbA-ubiquitin-IGF (i.e., DsbA lacking a signal sequence) with an expected size of approximately 37 kD, or with pDM15426, which expresses DsbA-Ubi-IGF in which DsbA retains its native signal sequence and has an expected size of approximately 37 kD.

FIG. 9 shows the results obtained with fusions to IGFBP-3. Panel [i] shows the ubiquitin-IGFBP-3 fusion, with an expected size of approximately 38 kD (pDJ12875); panel [ii], IL1-ubiquitin-IGFBP3, with an expected size of approximately 55 kD (pDM16967); and [iii], DsbA-ubiquitin-IGFBP-3, with an expected size of approximately 60 kD (pDM15427). Solubility was markedly higher for the fusion to IL-1.

FIG. 10, panel [i], shows whole cell lysates from 0 and 120 minute timepoints and "soluble" ("S") and "insoluble" ("I") fractions from E. coli cells expressing a ubiquitin-TGF-βR fusion with an expected size of approximately 24 kD (pDJ16921), panel [ii], a DsbA-ubiquitin-TGF-βR fusion with an expected size of approximately 46 kD (pDM15428; βR is the extracellular domain of the TGF-β receptor). The ubiquitin-TGF-βR fusion was largely insoluble. In marked contrast, the DsbA-ubiquitin-TGF-βR fusion was virtually completely soluble.

Example 5: Biological activity of human IGF-I obtained from fusion proteins in bacterial cells crown at 37° C.

Figure 11:
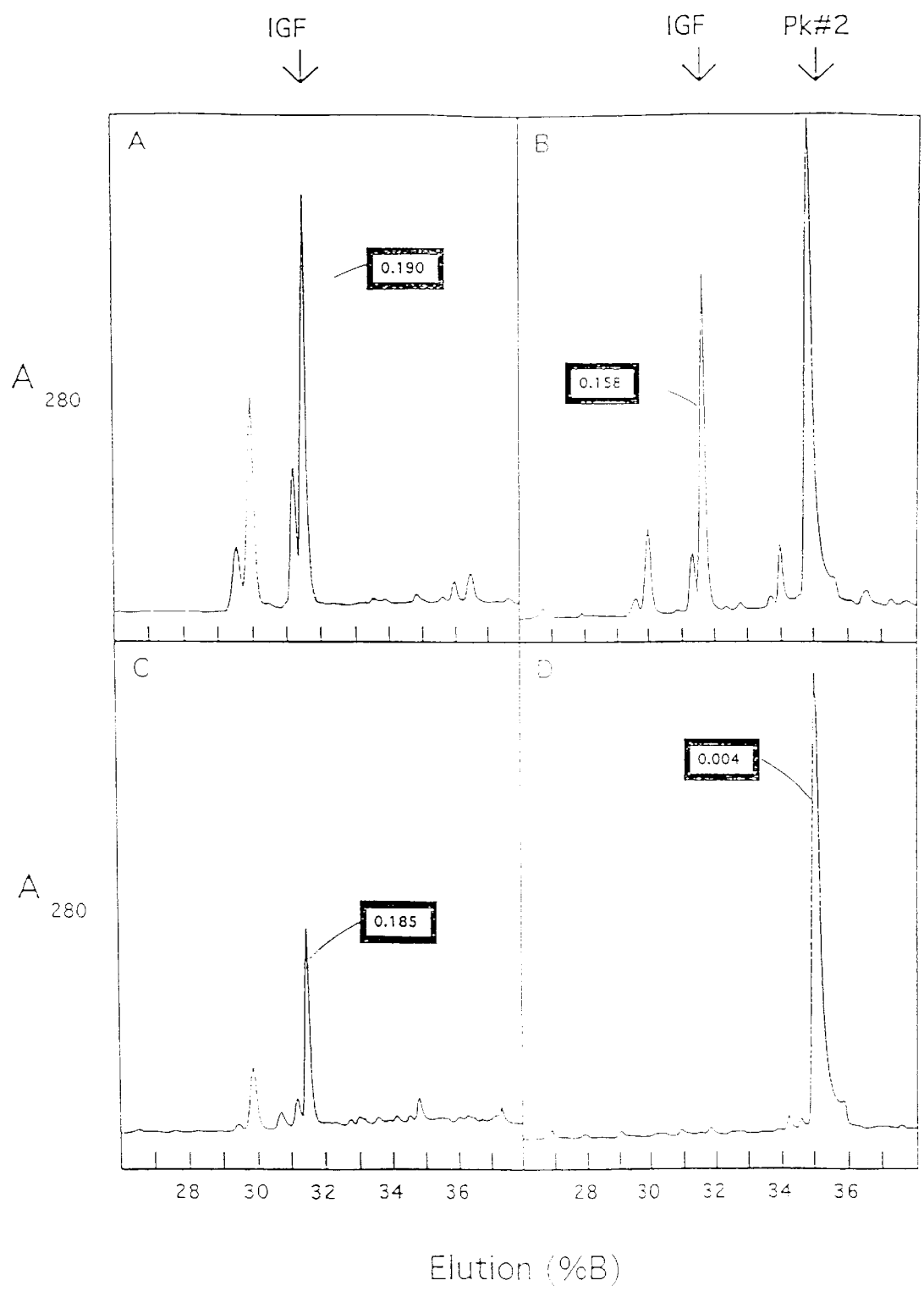

FIG. 11 shows the effects of temperature and of fusion to DsbA polypeptide on the in vivo folding of IGF-I into a biologically active conformation.

The fusion proteins were purified from extracts of these cultures by passing "soluble" fractions prepared from 100 ml of induced cells as described above ("simple sonication protocol") over a Q-Sepharose (Pharmacia) column (5 ml bed volume) equilibrated in 50 mM Tris-Cl, pH 8.0, 1 mM EDTA. The column was washed in two column volumes of the same buffer, and the sample was eluted in 8 ml of the same buffer with an additional 0.4M NaCl. The eluate was concentrated on a Centricon-30 membrane (Amicon) to a volume of 0.5 ml.

Ubipuitin hydrolase cleavage. To the above concentrate was added 10 µl of crude extract of ubiquitin hydrolase enzyme, which was prepared from a strain containing plasmid 23344 as described below in Example 6.

HPLC-reverse phase chromatography. HPLC-reverse phase chromatography was performed as follows. After incubation with ubiquitin hydrolase for 60 minutes at 37° C., the digest was directly applied to a C-18 (Vydac) reverse phase column and subjected to HPLC chromatography in a two-buffer system: Buffer A was aqueous 0.1% trifluoroacetic acid (TFA) and Buffer B was 0.1% TFA in acetonitrile. The column was developed as follows: 0–22% B in 4 minutes; wash in 22% B for 6 minutes; elute in a 22–42% B gradient at 0.5% per minute (40 minutes total). The IGF-I standard elutes at 31.4% B under these conditions. Peaks were collected, then diluted for the IGF bioassay (below), or subjected to PAGE analysis. The peak collected from the 31.4% position in all samples contained a single protein band migrating at 7.5 kD as determined by PAGE, with the protein band visualized by silver staining. No contaminating proteins were observed in this fraction. Peak heights were therefore used to estimate the amount of IGF present by comparison with a commercial IGF standard.

IGF Bioassay. In the IGF bioassay, MG63 cells (ATCC CRL #1427, a male osteosarcoma cell line) were plated in 96-well microtiter plates at 5000 cells per well and incubated for 16 hours at 37° C. in a $CO_2$ incubator. The culture medium was aspirated and samples (including commercial IGF standards, such as are available from Imcera, Terre Haute, Ind.) were added to the wells in RPMI medium, 2 mM glutamine, 50 U/ml penicillin, 50 mcg/ml streptomycin, 0.05% bovine serum albumin (BSA).

Serial two-fold dilutions of each sample were tested. Using Cell Proliferation Kit (catalog no. RPN.210, Amersham) cells were incubated for 24 hours at 37° C., the medium was decanted, and 100 µl of the kit's labelling reagent was diluted as directed in the same medium and was added to each well. The plates were then incubated at 37° C. for three hours.

After the reagent was decanted, the cells were washed in cold PBS three times then fixed by the addition of 100 µl 90% ethanol, 5% acetic acid to each well. The fixed cells were incubated for 30 minutes at room temperature, then washed three times each in (a) PBS+0.1% Tween-20; (b) PBS+0.1% Triton X-100, and (c) PBS+0.1% Tween-20. Subsequently, the wells were blocked for 15 minutes at room temperature in PBS+0.1% Tween-20+1% nonfat dry milk (NFDM, Carnation brand) and treated with the antibody label provided in the kit according to the manufacturer's protocol (Amersham). The $A_{405}/A_{490}$ ratio was measured in order to determine 5-bromo-2-dioxyuridine (BRDU) incorporation. The concentration of IGF-I in each sample was determined by comparison with a standard curve. All samples were assayed in triplicate.

Following the binding reaction, samples were chemically cross-linked by addition of 0.3 mM disuccinimidyl suberate at 4° C. for 30 minutes. Cross-linking was terminated by adding Tris-HCl, pH 7.5, to a concentration of 20 mM, followed by boiling for 10 minutes. A portion of the cross-linked sample was enzymatically deglycosylated by incubation with N-glycosidase F at 37° C. for three hours in the presence of 0.2% 2-mercaptoethanol and 2% SDS. Following this incubation, a second aliquot of N-glycosidase F was added, and the sample was incubated further for one hour. The products of the binding reaction were separated by SDS-PAGE under reducing conditions using a 8% gel. The labeled species were visualized after fixation of the gel in 10% acetic acid, 40% methanol by autoradiography.

FIGS. 11A and 11B show HPLC-reverse phase elution profiles from ubiquitin hydrolase-cleaved IGF-I derived from cultures of DsbA-ubiquitin-IGF and ubiquitin-IGF constructs, respectively, grown at 30° C. FIGS. 11C and 11D show the corresponding data from cultures of DsbA-ubiquitin-IGF and ubiquitin-IGF constructs, respectively, grown at 37° C. The position of IGF-I at 31.4% buffer B was established by comparison with a commercial purified IGF standard. It is clear in FIG. 11D that at 37° C. the ubiquitin fusion did not produce properly folded IGF-I (IGF-I is at about 35% B), but the ubiquitin fusion produced properly folded IGF-I at 30° C. Although the temperature dependence of IGF-I folding per se was not unexpected, the marked effect of a DsbA fusion partner on the recovery of properly folded IGF-I was surprising (compare FIGS. 11C and 11D).

The specific activity of the IGF peaks (shown in FIG. 11 as boxed values, arbitrary units) was established by the IGF bioassay. In this assay the specific activity of authentic IGF-I was 0.206. In contrast, the specific activity of peak #2, the major peak in FIG. 11D (ubiquitin fusion, 37° C.), was 0.004.

The amino-terminal protein sequence for the IGF-I peak in FIG. 11C was established by Edman degradation in an automated sequencer (Applied BioSystems, Foster City, Calif.). A single major species was recovered with the sequence Gly-Pro-Glu-Thr-Leu-X-Gly-Ala-Glu-Leu (SEQ ID NO:9). This was the expected amino terminal sequence for mature IGF-I and shows, additionally, that ubiquitin hydrolase cleaved as precisely as expected.

To exclude the unlikely possibility that the purification of the IGF-I sample prior to HPLC might have influenced the results, crude extracts ("soluble" fraction) from strains carrying the constructs listed in Table 4 were treated with ubiquitin hydrolase, adjusted for total protein concentration and diluted for the IGF bioassay. Cleavage of the fusion protein was confirmed by SDS-PAGE in each case. The crude bioactivities (in arbitrary units) were:

TABLE 4

Bioactivity of DsbA Fusion Proteins Cleaved With Ubiquitin Hydrolase

| CONSTRUCT | FUSION | BIOACTIVITY |
| --- | --- | --- |
| pDM16927 | Ubiquitin-IGF | 0.113 ± 0.009 |
| pDM15422 | (SS−) DsbA-ubiquitin-IGF | 0.368 ± 0.030 |
| pDM15426 | (SS+) DsbA-ubiquitin-IGF | 0.242 ± 0.018 |

These results confirmed the earlier observation that a DsbA fusion partner substantially increases the recovery of biologically active IGF-I from E. coli. Bioactive IGF-I was also obtained and analyzed in a similar fashion from fusions containing IL-1-β in place of DsbA. The IGF-I-DsbA fusions obtained also displayed the correct amino-terminal sequence (GPETLXGA . . . ) after cleavage with ubiquitin hydrolase.

Taken together, these results demonstrate the utility of IL-1-like fusion partners in the production, accumulation and recovery of biologically active IGF-I in bacterial cells.

Example 6: Production of yeast ubiguitin hydrolase in bacterial cells and co-expression of fusion polypeptides.

Ubiquitin hydrolase (UH) expression vectors were derived from a cDNA clone of UBP-1 (Tobias and Varshavsky, J. Biol. Chem. 266:12021–12028, 1991) by deleting the amino-terminal 92 codons of the gene upstream of the unique BglII site and replacing this DNA with (a) the first 12 codons of the phi-10 gene of bacteriophage T7, to yield plasmid 23344; (b) the 153 codons of mature human IL-1-β, followed by a linker encoding Asp-Arg-Gly-Asp-Pro-His-His-His-His-His-His-Glu (SEQ ID NO:11), to produce plasmid 23399; or (c) the 189 codons of E. coli DsbA, followed by a linker encoding His-His-His-His-His-His-Ser (SEQ ID NO:7), followed by the first 75 codons (after methionine) of yeast ubiquitin, followed by a linker encoding Asp-Pro-His-His-His-His-His-His-Glu (SEQ ID NO:12), to yield plasmid 27246. In each case, the in-frame fusions resulted in a fusion gene under the control of the T7 promoter. The vector backbone and other details of the transcriptional unit used in these experiments are described in Example 1.

Cells of E. coli strain W3110 DE3 were transformed with combinations of compatible plasmids as follows:

TABLE 5

In vivo cleavage of IGF fusions by Ubiquitin Hydrolase (UH)

| STRAIN | PLASMIDS | DESCRIPTION | RESULTS |
| --- | --- | --- | --- |
| #1 | 23999 + 15426 | Il-1-UH + (SS+)DsbA-ubi-IGF | Minimal cleavage of IGF fusion |
| #2 | 27246 + 15426 | DsbA-ubi-UH + (SS+)DsbA-ubi-IGF | No cleavage |
| #3 | 27246 + 22070 | DsbA-ubi-UH + (SS−)DsbA-ubi-IGF | Cleavage virtually complete |
| #4 | 23344 + 15422 | phiIO-UH + (SS−)DsbA-ubi-IGF | Cleavage virtually complete |

After induction with IPTG as described in Example 1, major bands appeared on Coomassie-stained SDS-polyacrylamide gels which corresponded to the expected sizes of IGF fusion protein and the product of its cleavage with UH.

The results shown in Table 5 clearly demonstrate that a protein fusion targeted to the periplasmic space via the general secretion pathway is relatively immune to cleavage by UH enzyme fused to either IL-1-β or DsbA, but the identical fusion protein sequestered via the alternative pathway used by mature DsbA (i.e., lacking a signal sequence) is effectively cleaved by either cytoplasmic or DsbA-fused UH enzyme. Despite the selective extraction observed for IL-1-like polypeptides and their fusions when expressed in E. coli (Example 3), these polypeptides appear to be sequestered in a manner that is different from that of classical periplasmic proteins. These results also show that co-expressed ubiquitin hydrolase genes can efficiently cleave in vivo a fusion polypeptide comprising an IL-1-like polypeptide separated from a polypeptide of interest, such as IGF, by a linker containing a ubiquitin hydrolase cleavage site.

Example 7: Purification of TGF receptor fragment and cross-linking assay

The "soluble" fraction prepared from induced cells (100 ml culture volume) containing plasmid pDM15428 was passed over a 1 ml bed volume Ni-NTA affinity column (QIAGEN Inc., Chatsworth, Calif.), equilibrated, washed and developed according to the manufacturer's recommendations. The eluate was dialysed against the original loading buffer, digested with a partially pure preparation of ubiquitin hydrolase, and passed over an Ni-NTA column identical to that described above. The pass-through was concentrated on a Centricon-10 membrane (Amicon) to a final volume of 0.5 ml. and used for cross-linking assays as follows: 20 µl of this sample was incubated overnight with 100 µM $^{125}$I-TGF-β1 (250 nM). The sample was cross-linked with 0.3 mM disuccinimidyl suberate (Pierce Chemical, Rockford, Ill.) for 15 minutes at 4° C. The reaction was quenched by the addition of one-third volume of 4× Laemmli gel sample buffer containing 50 mM dithiothreitol. The sample was boiled for two minutes (100° C.) and subjected to SDS-PAGE. The gel was dried and visualized by autoradiography with overnight exposure at −80° C.

FIG. 12 shows the result of crosslinking experiments using $^{125}$I-radiolabeled TGF-β1 and partially purified TGF-βR (136 amino acid extracellular domain). The expected crosslinked product is observed migrating at about 30 kD. This product is formed by a specific binding interaction, because its appearance is completely abolished by the addition of (1000-fold molar) excess cold TGF-β1. These data show that with the aid of an IL-1-like fusion partner, functional TGF-β receptor can be produced in bacteria.

Example 8: IGFBP-3 Dot Blot Assay

For the IGFBP-3 dot blot assay, pre-cut Immobilon-P membrane (Millipore) was soaked in methanol for 5 seconds, rinsed with Tris-buffered saline (TBS), and then soaked in TBS for 10 minutes. The membrane was mounted on a dot blot apparatus and 50 μl TBS was applied to each well. The samples were applied to the membrane by vacuum suction. The membrane was then blocked in TBS +3% non-fat dry milk (CARNATION brand) at room temperature for two hours. $^{125}$I-radiolabelled IGF-I (1 μl per ml blocking buffer) was added, followed by incubation at room temperature for two hours. The buffer was discarded and the filter washed in TBS (2×15 minute washes at room temperature). The membrane was then air dried for ten minutes then exposed to Kodak XR-Omat film overnight at −80° C.

FIG. 13 shows the results of a dot-blot binding assay using $^{125}$I-radiolabeled IGF-I to measure binding activity in crude extracts ("soluble" fraction) of strains expressing (1) a DsbA-ubiquitin-IGFBP-3 fusion (pDM15427), (2) a ubiquitin-IGFBP-3 fusion (pDJ12875), or (3) a "vector only" control (pDJ12887). Similar results were obtained whether the samples were pretreated with ubiquitin hydrolase (+UH) or were not treated (−UH), indicating that the intact fusion proteins can bind the ligand as efficiently as the cleaved IGFBP-3 protein. In this case, no ubiquitin cleavage is necessary to obtain an active protein.

The results clearly show that the DsbA fusion partner increases the recovery of bioactive IGFBP-3 by about 16-fold (4-fold serial dilutions are used on the blot).

Example 9: Expression of IL-1-β-IGFBP-3 fusion protein in mammalian cells

Expression plasmid pDM15430, which encodes an IL-1-β-IGFBP3 fusion protein in mammalian cells, was constructed by inserting a fusion sequence from plasmid pDM16964 into pDJ12147, a deletion derivative of pRc-CMV (InVitrogen Corp, La Jolla, Calif.) which utilizes a human cytomegalovirus promoter and enhancer and bovine growth hormone polyadenylation signal. The fusion sequence from plasmic pDM16964 comprises codons for an initiator methionine, the 153 amino acids of mature human IL-1-β and the 264 amino acids of mature human IGFBP-3.

This construct and the corresponding non-recombinant plasmid ("vector") were used to transiently transfect COS-M6 cells using the DEAE-dextran method (Seed and Aruffo, Proc. Natl. Acad. Sci. U.S.A. 84:3365–3369, 1987). Cell extracts were made 72 hours after transfection by lysing the cell layer with phosphate buffered saline (PBS) containing 0.2% NP-40 at 4° C. for 30 minutes. The extract was centrifuged to remove insoluble debris, and the supernatant was used for binding assays.

FIG. 14 shows that endogenous IGF-binding activity was found in COS cell extracts in a broad band in the 45–50 kD size range (Y). FIG. 14, right, shows SDS-PAGE of cross-linked samples from COS cells transiently transfected as described above with pDM15430, which encodes IL1-IGFBP3 ("IL1-BP3"). FIG. 14, left, shows SDS-PAGE of cross-linked samples from COS cells transfected with the vector, alone ("vector"). Each set of gels has a left lane with no endoglycosidase F treatment or "cold" IGF competition. The middle lane shows results after treatment with endoglycosidase F, and the right lane shows the results of competition with an excess of "cold" IGF. After treatment of the crosslinked sample with endoglycosidase F as described above, the endogenous IGF binding band was reduced to a sharper band migrating at about 40 kD. In cells transfected with an IL-1-β-IGFBP-3 fusion construct, a crosslinked band in the expected size range (approximately 55 kD+, "X" in FIG. 14) was observed. However, treatment with endoglycosidase F did not alter the mobility of the X band. This demonstrates that the IL1β-IGFBP-3 fusion protein that accumulated in these cells was not glycosylated. All of the binding observed was specific, as it was successfully competed away with cold IGF (see right lanes of FIG. 14).

In parallel experiments, cells transfected with Met-IGFBP-3 constructs lacking the IL-1 fusion partner did not show any detectable IGF binding by the above criteria (data not shown). Other experiments have shown that the natural form of the IGFBP-3 gene (i.e., with its own signal sequence) produces a glycosylated product in mammalian cells (Spratt et al., *Growth Factors* 3:63–72, 1990). Thus, the IL-1 fusion of the present example is likely to be sequestered in the mammalian cell (as is IL-1-β itself), but not by virtue of passage through the ER and Golgi, the normal route taken by secreted proteins which would result in glycosylation of the IGFBP-3 protein.

All publications and patent applications mentioned in this specification are incorporated herein by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

We claim:

1. A nucleic acid encoding a fusion protein or polypeptide, said fusion polypeptide comprising a polypeptide of the beta-trefoil fold structural family selected from the group consisting of int-2, hst/KS3, keratinocyte growth factor, hisactophilin and soybean trypsin inhibitor, a linker peptide, and a protein or polypeptide of interest, wherein said linker peptide is positioned between said polypeptide of the beta-trefoil fold structural family and said protein or polypeptide of interest and wherein said polypeptide of the beta-trefoil fold structural family constitutes the amino terminus of said fusion protein or polypeptide and lacks a signal sequence.

2. A nucleic acid according to claim 1 wherein said linker peptide comprises a polypeptide cleavage site.

3. A nucleic acid according to claim 2 wherein said linker peptide comprises a ubiquitin molecule.

4. An expression vector comprising a nucleic acid according to claim 1.

5. A host cell comprising a nucleic acid according to claim 1.

6. A host cell comprising:
  an expression vector capable of expression in said host cell a fusion protein or polypeptide, said fusion protein or polypeptide comprising a polypeptide of the beta-trefoil fold structural family selected from the group consisting of int-2, hst/KS3, keratinocyte growth factor, hisactophilin and soybean trypsin inhibitor, a linker peptide comprising a proteolytic enzyme cleavage site, and a protein or polypeptide of interest, wherein said linker peptide is positioned between said beta-trefoil fold structural family polypeptide and said protein or polypeptide of interest and further wherein said beta-trefoil fold structural family polypeptide constitutes the amino terminus of said fusion protein or polypeptide and lacks a signal sequence; and
  a nucleic acid capable of expressing in the cytoplasm of a host cell a proteolytic enzyme which specifically recognizes said proteolytic enzyme cleavage site.

7. A host cell according to claim 6 wherein said proteolytic enzyme is ubiquitin hydrolase and said proteolytic enzyme cleavage site is a ubiquitin molecule.

8. A fusion protein or polypeptide comprising a polypeptide of the beta-trefoil fold structural family selected from the group consisting of int-2, hst/KS3, keratinocyte growth factor, hisactophilin and soybean trypsin inhibitor, , a linker peptide, and a protein or polypeptide of interest, wherein said linker peptide is positioned between said beta-trefoil fold structural family polypeptide and said protein or polypeptide of interest and wherein said beta-trefoil fold structural family polypeptide constitutes the amino terminus of said fusion protein or polypeptide and lacks a signal sequence.

9. A fusion protein or polypeptide according to claim 8 wherein said linker peptide comprises a proteolytic enzyme cleavage site.

10. A fusion protein or polypeptide according to claim 9 wherein said linker peptide comprises a ubiquitin molecule.

11. A fusion protein or polypeptide according to claim 8 wherein said protein or polypeptide of interest comprises an enzyme, a growth factor, or an antibody, a DNA binding protein, an RNA binding protein, or a membrane receptor.

12. A method of producing a fusion protein or polypeptide comprising a polypeptide of the beta-trefoil fold structural family selected from the group consisting of int-2, hst/KS3, keratinocyte growth factor, hisactophilin and soybean trypsin inhibitor, , and a protein or polypeptide of interest, wherein said polypeptide of the beta-trefoil fold structural family constitutes the amino terminus of said fusion protein or polypeptide and lacks a signal sequence, said method comprising the steps of:

introducing a nucleic acid encoding said fusion protein or polypeptide into a host cell, thereby producing a transformed host cell;

culturing said transformed host cell under conditions appropriate for expressing said fusion protein or polypeptide; and purifying said fusion protein or polypeptide.

13. A method of producing a protein or polypeptide of interest, said method comprising the steps of:

introducing into a host cell a nucleic acid encoding a fusion protein or polypeptide, said fusion protein or polypeptide comprising a polypeptide of the beta-trefoil fold structural family selected from the group consisting of int-2, hst/KS3, keratinocyte growth factor, hisactophilin and soybean trypsin inhibitor , a linker peptide, and a protein or polypeptide of interest wherein said linker peptide is positioned between said polypeptide of the beta-trefoil fold structural family and said protein or polypeptide of interest and encodes a proteolytic cleavage site and said polypeptide of the beta-trefoil fold structural family constitutes the amino terminus of said protein or polypeptide and lacks a signal sequence, thereby producing a transformed host cell;

culturing said transformed host cell under conditions appropriate for expressing said fusion protein or polypeptide, thereby expressing said fusion protein or polypeptide;

cleaving said fusion protein or polypeptide with a proteolytic enzyme which recognizes said proteolytic cleavage site, thereby producing said protein or polypeptide of interest; and purifying said protein or polypeptide of interest.

14. The method according to claim 13 wherein said proteolytic enzyme is ubiquitin hydrolase and said proteolytic enzyme cleavage site is a ubiquitin molecule.

15. A method of producing a protein or polypeptide of interest comprising the steps of:

introducing into a host cell a nucleic acid encoding a fusion protein or polypeptide, said fusion protein or polypeptide comprising a polypeptide of the beta-trefoil fold structural family selected from the group consisting of int-2, hst/KS3, keratinocyte growth factor, hisactophilin and soybean trypsin inhibitor, , a linker peptide, and a protein or polypeptide of interest, wherein said linker peptide is positioned between said polypeptide of the beta-trefoil fold structural family and said protein or polypeptide of interest and encodes a proteolytic enzyme cleavages site and wherein said polypeptide of the beta-trefoil fold structural family constitutes the amino terminus of said fusion protein or polypeptide and lacks a signal sequence;

said host cell comprising a nucleic acid capable of expressing in the cytoplasm of said host cell a proteolytic enzyme which specifically recognizes said proteolytic enzyme cleavage site, thereby producing a transformed host cell;

culturing said transformed host cell under conditions appropriate for expressing said fusion protein or polypeptide and said proteolytic enzyme, thereby expressing said fusion protein or polypeptide and causing the in vivo cleavage of said fusion protein or polypeptide and producing said protein or polypeptide of interest; and purifying said protein or polypeptide of interest.

16. The method according to claim 15 wherein said proteolytic enzyme is ubiquitin hydrolase and said proteolytic enzyme cleavage site is a ubiquitin molecule.

* * * * *